US012049490B2

(12) United States Patent
Yamada-Hunter et al.

(10) Patent No.: US 12,049,490 B2
(45) Date of Patent: Jul. 30, 2024

(54) SOLUBLE LEUKEMIA INHIBITORY FACTOR RECEPTOR POLYPEPTIDES AND METHODS OF USING SAME FOR INHIBITING LEUKEMIA INHIBITORY FACTOR ACTIVITY

(71) Applicant: The Board of Trustees of the Leland Stanford Junior University, Stanford, CA (US)

(72) Inventors: Sean Yamada-Hunter, Stanford, CA (US); Jennifer R. Cochran, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 559 days.

(21) Appl. No.: 17/260,473

(22) PCT Filed: Jul. 19, 2019

(86) PCT No.: PCT/US2019/042648
§ 371 (c)(1),
(2) Date: Jan. 14, 2021

(87) PCT Pub. No.: WO2020/018932
PCT Pub. Date: Jan. 23, 2020

(65) Prior Publication Data

US 2021/0300992 A1 Sep. 30, 2021

Related U.S. Application Data

(60) Provisional application No. 62/701,399, filed on Jul. 20, 2018.

(51) Int. Cl.

| | |
|---|---|
| ***C07K 14/715*** | (2006.01) |
| ***A61K 38/00*** | (2006.01) |
| ***A61P 35/00*** | (2006.01) |

(52) U.S. Cl.
CPC ............ *C07K 14/715* (2013.01); *A61P 35/00* (2018.01); *C07K 14/7155* (2013.01); *A61K 38/00* (2013.01); *C07K 2319/30* (2013.01)

(58) Field of Classification Search
CPC .............. C07K 14/715; C07K 14/7155; C07K 2319/30
See application file for complete search history.

(56) References Cited

U.S. PATENT DOCUMENTS

| | | | | |
|---|---|---|---|---|
| 5,284,755 A * | 2/1994 | Gearing | A61P 3/06 435/69.7 |
| 6,387,875 B1 | 5/2002 | Nicola et al. | |
| 2010/0223684 A1 | 9/2010 | Matsuoka et al. | |

FOREIGN PATENT DOCUMENTS

| | | | |
|---|---|---|---|
| WO | 1992010570 | 6/1992 | |
| WO | 1993010151 | 5/1993 | |
| WO | 1998048011 | 10/1998 | |
| WO | 2018015539 | 1/2018 | |
| WO | WO2018029586 * | 2/2018 | C07K 16/00 |

OTHER PUBLICATIONS

Aasland et al. (2002) "The upper cytokine-binding module and the Ig-like domain of the leukaemia inhibitory factor (LIF) receptor are sufficient for a functional LIF receptor complex" Journal Of Molecular Biology, 315(4):637-646.
Hunter et al. (2021) "An engineered ligand trap inhibits leukemia inhibitory factor as pancreatic cancer treatment strategy" Communications Biology, 4(1):XP055901337.
Owczarek et al. (1997) "The Unusual Species Cross-reactivity of the Leukemia Inhibitory Factor Receptor [alpha]-Chain Is Determined Primarily by the Immunoglobulin-like Domain" Journal Of Biological Chemistry, 272(38):23976-23985.
Bravo et al. (1998) "Crystal Structure of a Cytokine-Binding Region of gp130" The EMBO Journal, 17(6):1665-1674.
Gearing et al. (1991) "Leukemia Inhibitory Factor Receptor is Structurally Related to the IL-6 Signal Transducer, gp 130" The EMBO Journal, 10(10):2839-2848.
Hunter and Cochran (2016) "Cell-Binding Assays for Determining the Affinity of Protein-Protein Interactions: Technologies and Considerations" Methods Enzymol. 580:21-44.
Bitard et al. (2003) "Mutations in the Immunoglobulin-like Domain of gp190, the Leukemia Inhibitory Factor (LIF) Receptor, Increase or Decrease Its Affinity for LIF" The Journal of Biological Chemistry, 278(18):16253-16261.
Fairlie et al. (2004) "Affinity Maturation of Leukemia Inhibitory Factor and Conversion to Potent Antagonists of Signaling", The Journal of Biological Chemistry, 279(3):2125-2134.
Timmermann et al. (2002) "A functional role of the membrane-proximal extracellular domains of the signal transducer gp130 in heterodimerization with the leukemia inhibitory factor receptor" Eur. J. Biochem. 269:2716-2726.

* cited by examiner

*Primary Examiner* — Elly-Gerald Stoica
(74) *Attorney, Agent, or Firm* — Brian E. Davy; Bozicevic, Field & Francis LLP

(57) ABSTRACT

Provided are soluble leukemia inhibitory factor receptor (LIFR) polypeptides, soluble glycoprotein 130 (gp130) polypeptides, and soluble fusion proteins and dimers including such polypeptides. The soluble polypeptides bind to leukemia inhibitory factor (LIF). In certain aspects, the soluble polypeptides exhibit increased binding affinity for LIF relative to the corresponding wild-type polypeptides. Also provided are nucleic acids encoding such soluble polypeptides, expression vectors including such nucleic acids, and cells including such nucleic acids and/or expression vectors. Methods of using the soluble polypeptides, including methods of inhibiting LIF activity in an individual in need thereof (e.g., to treat cancer), are also provided.

15 Claims, 21 Drawing Sheets

Specification includes a Sequence Listing.

| Sort Origin | Score | Variant | I217 | L218 | H240 | N242 | N242 | I257 | I260 | V262 | T273 | N277 | # Muts |
|---|---|---|---|---|---|---|---|---|---|---|---|---|---|
| 3 | 16.9 | PRVAID | | P | R | | | V | | A | I | D | 6 |
| 5 | 15.78 | PRDSAID | | P | R | | D | | | A | I | D | 7 |
| 3 | 15.59 | PVAID | | P | | | | V | | A | I | D | 5 |
| 5 | 14.37 | VPDAID | V | P | | | D | | | A | I | D | 6 |
| 4 | 13.89 | PVVIDN | | P | | | | V | V | | I | D | 6 |
| 4 | 13.42 | PSVID | | P | | S | | | V | | I | D | 5 |
| 3 | 13.31 | PAID | | P | | | | | | A | I | D | 4 |
| 3 | 13.23 | VPSID | V | P | | S | | | | | I | D | 5 |
| 2 | 12.21 | PID | | P | | | | | V | | I | D | 4 |
| 4 | 11.32 | L8M | | P | R | | | | | | I | D | 8 |
| - | 7.71 | PDD | | P | | | D | V | | | | D | 4 |
| - | 1.32 | WT | | | | | | | | | | | 0 |

A

| Variant | I217 | L218 | H240 | N242 | N242 | I257 | I260 | V262 | T273 | N277 | # Muts |
|---|---|---|---|---|---|---|---|---|---|---|---|
| PR V AID | | P | R | | | V | | A | I | D | 6 |
| PR VVAID | | P | R | | | V | V | A | I | D | 7 |
| PRDVVAID | | P | R | | D | V | V | A | I | D | 8 |
| VPR VVAID | V | P | R | | | V | V | A | I | D | 7 |
| VPRDVVAID | V | P | R | | D | V | V | A | I | D | 9 |
| VP D AID | V | P | | | D | | | A | I | D | 6 |
| VP DVVAID | V | P | | | D | V | V | A | I | D | 8 |
| PRD AID | | P | R | | D | | | A | I | D | 7 |
| P DV D | | P | | | D | V | | | | D | 4 |
| WT | | | | | | | | | | | 0 |

B

A

| Sort Origin | Score | Variant | E4 | K5 | N14 | K45 | F46 | K83 | Y95 | N100 | I130 | K184 | # Muts |
|---|---|---|---|---|---|---|---|---|---|---|---|---|---|
| 5 | 23.59 | ELRDSLE | | | | E | L | R | D | S | | E | 7 |
| 2 | 23.01 | EDE | | | | E | | | D | | | E | 3 |
| 3 | 22.14 | ELRDM | | | | E | L | R | D | | M | | 5 |
| 3 | 21.88 | ELDSM | | | | E | L | | D | S | M | | 5 |
| - | 16.00 | 8M | K | R | D | E | L | R | D | S | | | 8 |
| 4 | 15.92 | ELDI | | | | E | L | | D | | | | 4 |
| - | 1.03 | WT | | | | | | | | | | | 0 |

B

E D E
↓
ELD E
↓
ELDME

C

A

B

A

B

A

B

A

B

A

B

C

D

E

A

SOLUBLE LEUKEMIA INHIBITORY FACTOR RECEPTOR POLYPEPTIDES AND METHODS OF USING SAME FOR INHIBITING LEUKEMIA INHIBITORY FACTOR ACTIVITY

CROSS-REFERENCE TO RELATED APPLICATIONS

This application is a 371 national phase entry of International Patent Application No. PCT/US2019/042648, filed on Jul. 19, 2019, which claims the benefit of U.S. Provisional Patent Application No. 62/701,399, filed Jul. 20, 2018, which application is incorporated herein by reference in its entirety.

INTRODUCTION

Leukemia inhibitory factor (LIF) is a multi-functional cytokine which belongs to the IL-6 superfamily. Other members in the IL-6 superfamily include oncostatin M (OSM), IL-6, IL-11, ciliary neurotrophic factor (CNTF), and cardiotrophin-1 (CT-1). The LIF gene is highly conserved between humans and mice (about 75%). LIF protein is a monomeric protein which is often modified by glycosylation. The molecular weight of the unglycosylated LIF protein is 20-25 kDa, while the molecular weight of the glycosylated protein is in the range of 37-63 kDa.

LIF functions through both autocrine and paracrine manners. LIF binds to its specific receptor (leukemia inhibitory factor receptor—LIFR), then recruits glycoprotein 130 (gp130) to form a high affinity receptor complex that induces the activation of downstream signal pathways including the JAK/STAT3 signaling pathway (FIG. 1).

LIF plays a role in tumor development and progression. In contrast to its role in inhibiting the growth of leukemia cells, LIF often promotes the development and progression of many types of solid tumors. Overexpression of LIF promotes the proliferation of cultured human cancer cells and increases the growth of xenograft tumors formed by various human tumor cells. In addition, LIF increases the migration and invasiveness of tumor cells, and promotes metastasis of breast cancers and rhabdomyosarcomas. Hypoxia plays a critical role in LIF overexpression in solid tumors. Cytokines such as IL-6 and IL-1β can also induce LIF expression.

In addition, LIF is an emerging factor in pancreatic cancer. Recent studies demonstrate that inhibition of LIF in pancreatic cancer models—either through genetic manipulation or via antibody inhibition—improves life span of mice, decreases tumor burden, and limits tumor initiation. Despite being one of the deadliest cancers, there is a dearth of therapeutic options for pancreatic cancer. Current methods of inhibiting LIF employ Anti-LIF antibodies. However, antibodies are only able to target one specific face of LIF and therefore cannot fully compete with receptor binding. Further, the affinity of the endogenous interaction of LIF with its receptors is very high (~50-100 pM), a level of affinity difficult to truly compete with using an antibody alone. Improved ways of targeting LIF and inhibiting LIF activity/signaling are therefore needed.

SUMMARY

Provided are soluble leukemia inhibitory factor receptor (LIFR) polypeptides, soluble glycoprotein 130 (gp130) polypeptides, and soluble fusion proteins and dimers including such polypeptides. The soluble polypeptides bind to leukemia inhibitory factor (LIF). In certain aspects, the soluble polypeptides exhibit increased binding affinity for LIF relative to the corresponding wild-type polypeptides. Also provided are nucleic acids encoding such soluble polypeptides, expression vectors including such nucleic acids, and cells including such nucleic acids and/or expression vectors. Methods of using the soluble polypeptides, including methods of inhibiting LIF activity in an individual in need thereof (e.g., to treat cancer), are also provided.

Figure 10:
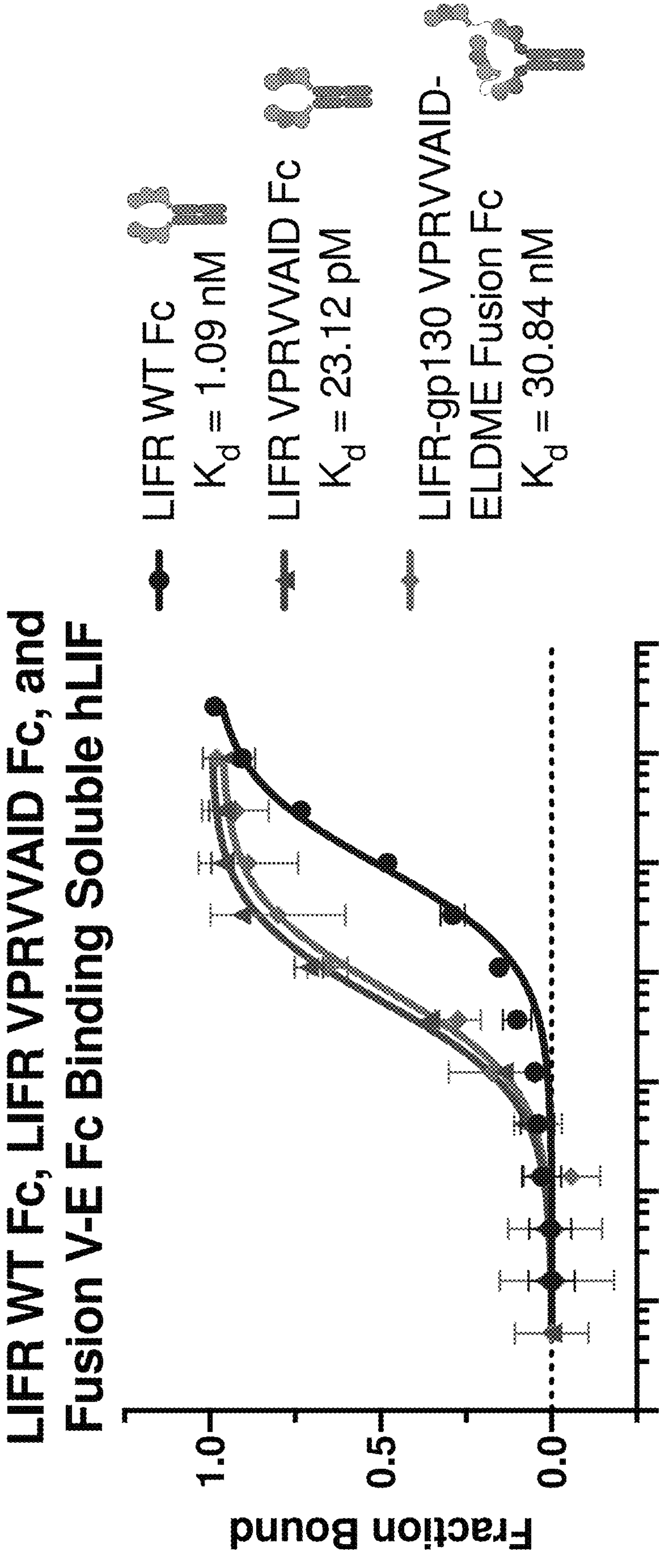

FIG. 10 Binding of purified LIF inhibitors. LIFR CBMI-Ig-like-CBMII wild-type Fc fusion (circles), LIFR CBMI-Ig-like-CBMII (VPRVVAID) Fc fusion (triangles), and LIFR CBMI-Ig-like-CBMII (VPRVVAID)—gp130 CBM (ELDME) Fc fusion (diamonds) binding to soluble human LIF, measured using KinExA. $K_D$ values calculated from by KinExA software as well as fitted curves are shown.

Figure 11:
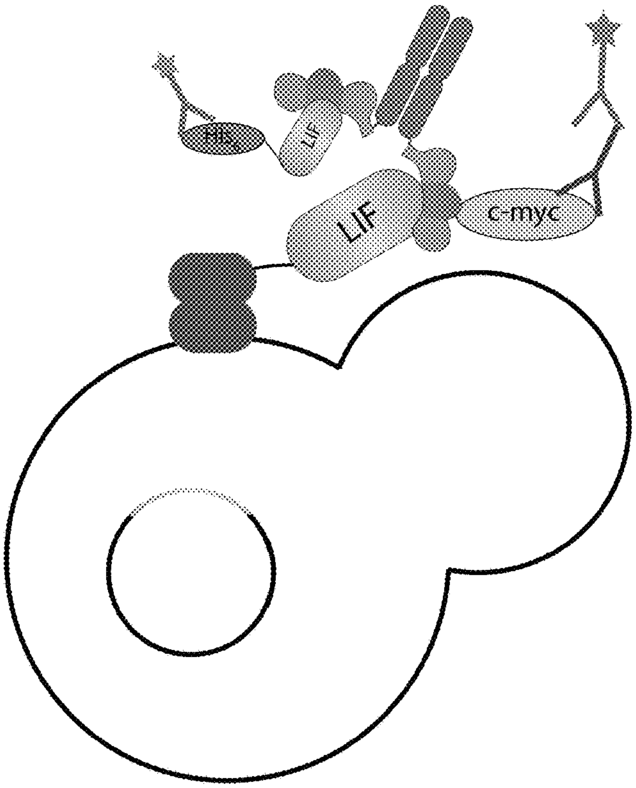
Figure 11:
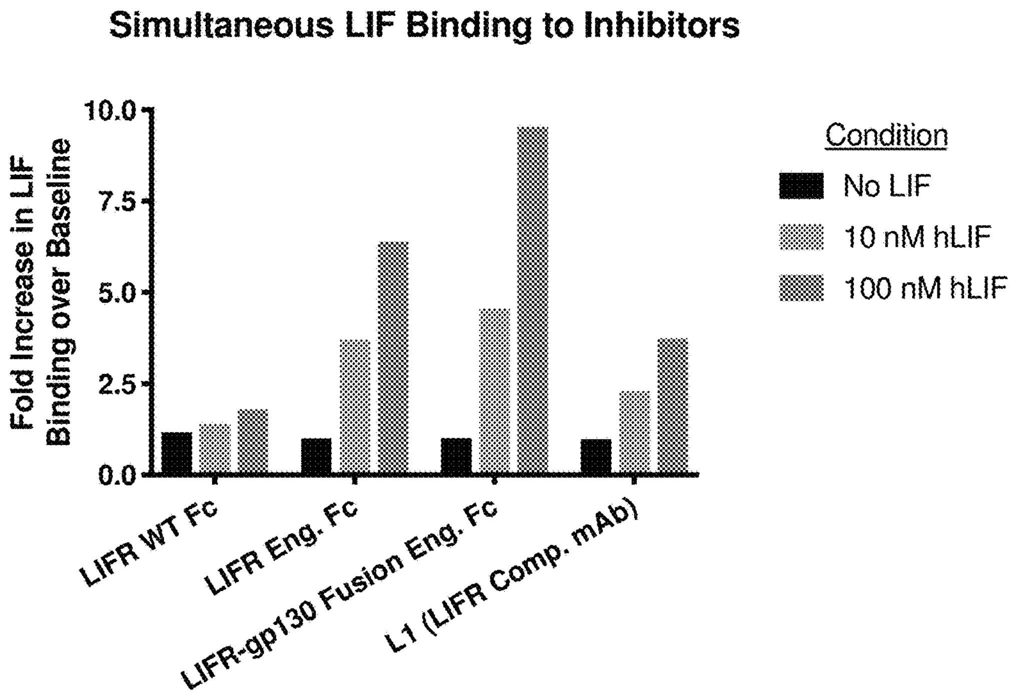

FIG. 11 Homodimeric LIF inhibitors bind multiple LIF's at once. Panel A: Schematic illustration of multiple LIF binding assay. LIF is displayed on the surface of yeast. Inhibitors are incubated at saturating concentrations and excess is washed away. LIF-His is then co-incubated with inhibitor-bound yeast at concentrations of 10 nM and 100 nM. Binding is detected via the His-tag domain of LIF, which should only be present if inhibitors are able to bind multiple LIF's at once, acting as a 'bridge.' Panel B: Results from multiple LIF binding experiment. LIF was displayed on yeast with LIFR-WT-Fc, LIFR-VPRVVAID-Fc, LIFR-gp130 Fusion-Fc, or the anti-LIF mAb, L1, used as a binding bridge between displayed and soluble LIF-His. Fluorescent emission from an anti-His fluorescent antibody in each condition was normalized to no LIF-His added controls.

Figure 12:
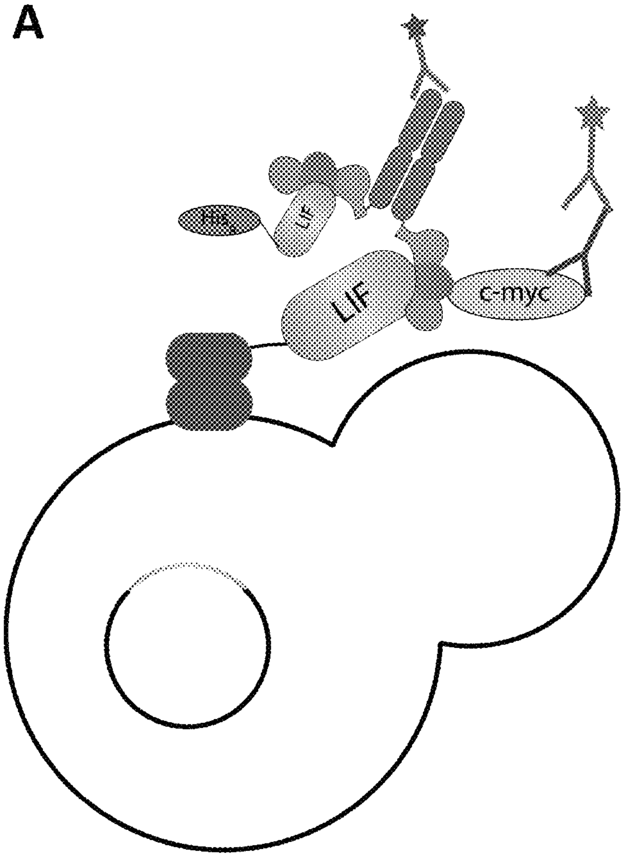
Figure 12:
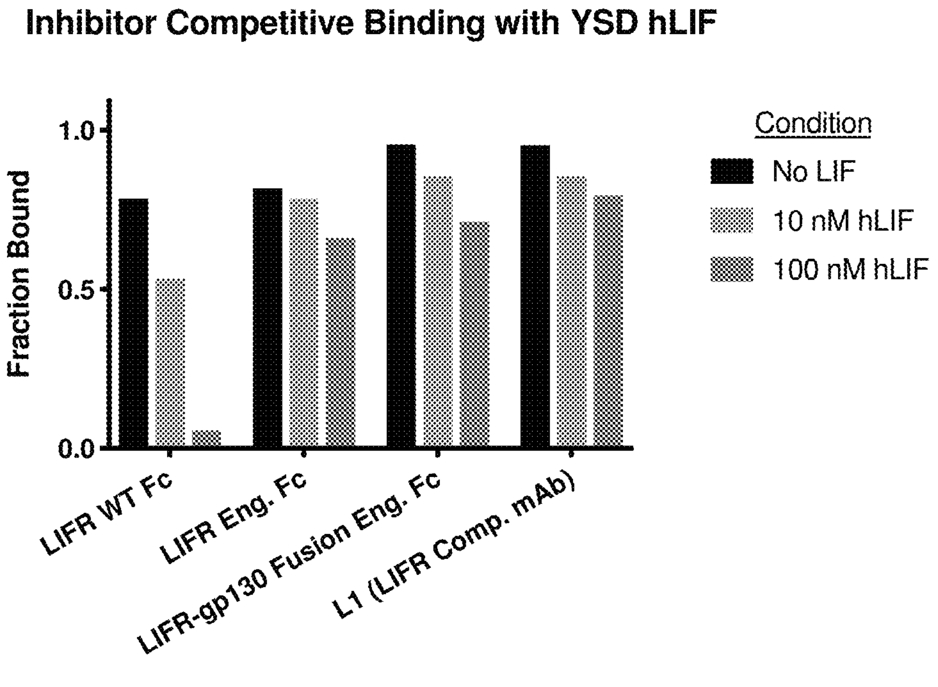

FIG. 12 Engineered inhibitors show improved off-rates when binding LIF in the presence of competitor when compared to WT. Panel A: Schematic illustration of competitive LIF binding assay. LIF is displayed on the surface of yeast. Inhibitors are incubated at saturating concentrations and excess is washed away. LIF-His is then co-incubated with inhibitor-bound yeast at concentrations of 10 nM and 100 nM. Binding is detected via the Fc domain of the inhibitor Fc-fusion, which will be competed away from the yeast-displayed LIF by high concentrations of soluble LIF-His. Panel B: Results from competitive LIF binding experiment. LIF was displayed on yeast with LIFR-WT-Fc, LIFR-VPRVVAID-Fc, LIFR-gp130 Fusion-Fc, or the anti-LIF mAb, L1 added as a binding partner. Excess inhibitor was washed away and soluble LIF was added as a competitor for 24 hours. Fluorescent emission from an anti-Fc fluorescent antibody in each condition was normalized to controls where excess inhibitor was not removed and soluble LIF was not added.

Figure 13:
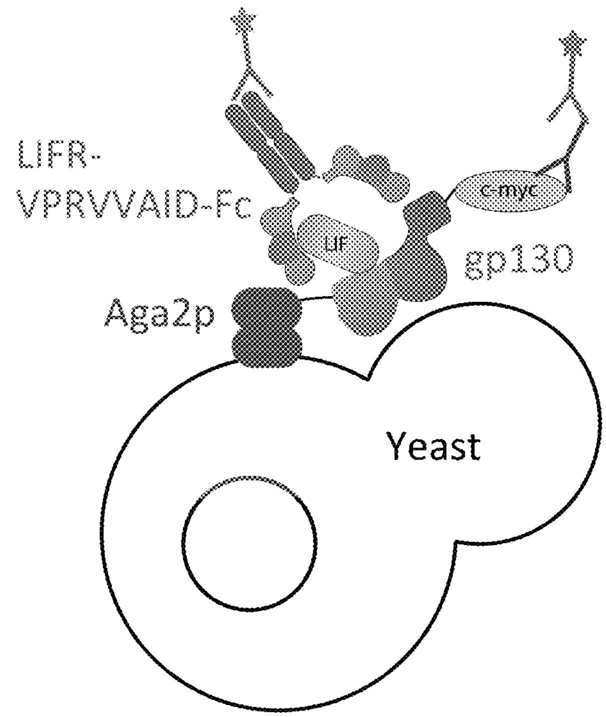
Figure 13:
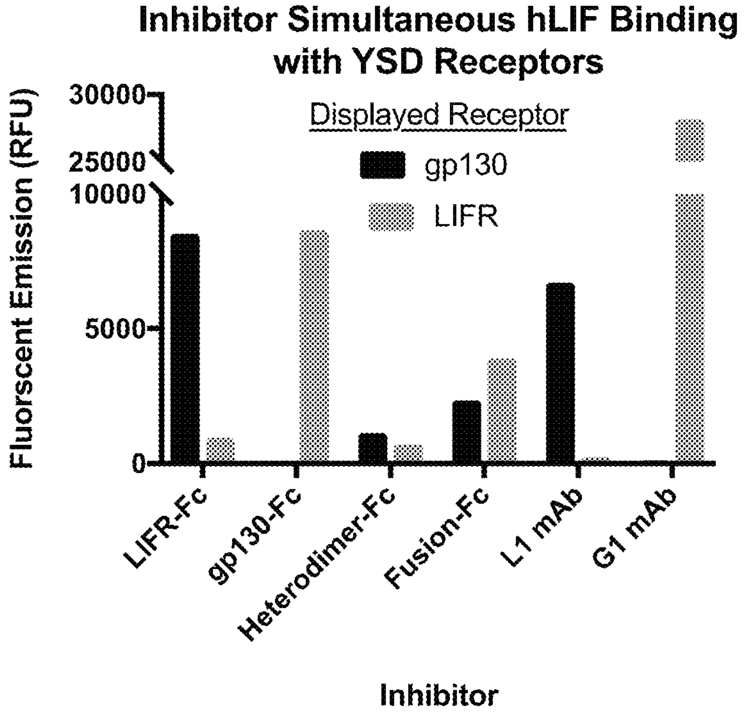

FIG. 13 LIF inhibitors bind LIF simultaneously. Panel A: Schematic illustration of simultaneous binding assay. Gp130 (depicted) or LIFR are displayed on the surface of yeast. LIF is incubated at saturating concentrations and excess is washed away. Inhibitors (LIFR-VPRVVAID-Fc depicted) are then co-incubated with LIF-bound yeast. Binding is detected via the Fc domain of the inhibitor, which should only be present if simultaneous receptor binding occurs, using LIF as a 'bridge.' Panel B: Results from simultaneous binding experiment. Either LIFR or gp130 were displayed on yeast with human LIF used as a binding bridge. Fluorescent emission is the readout of anti-Fc fluorescent antibody, normalized to no LIF added controls. Simultaneous binding of LIFR-VPRVVAID-Fc, gp130-ELDME-Fc, LIFR-gp130 heterodimeric Fc, LIFR-gp130 homodimeric Fusion-Fc, Anti-LIF mAb L1, and Anti-LIF mAb G1 are shown.

Figure 14:
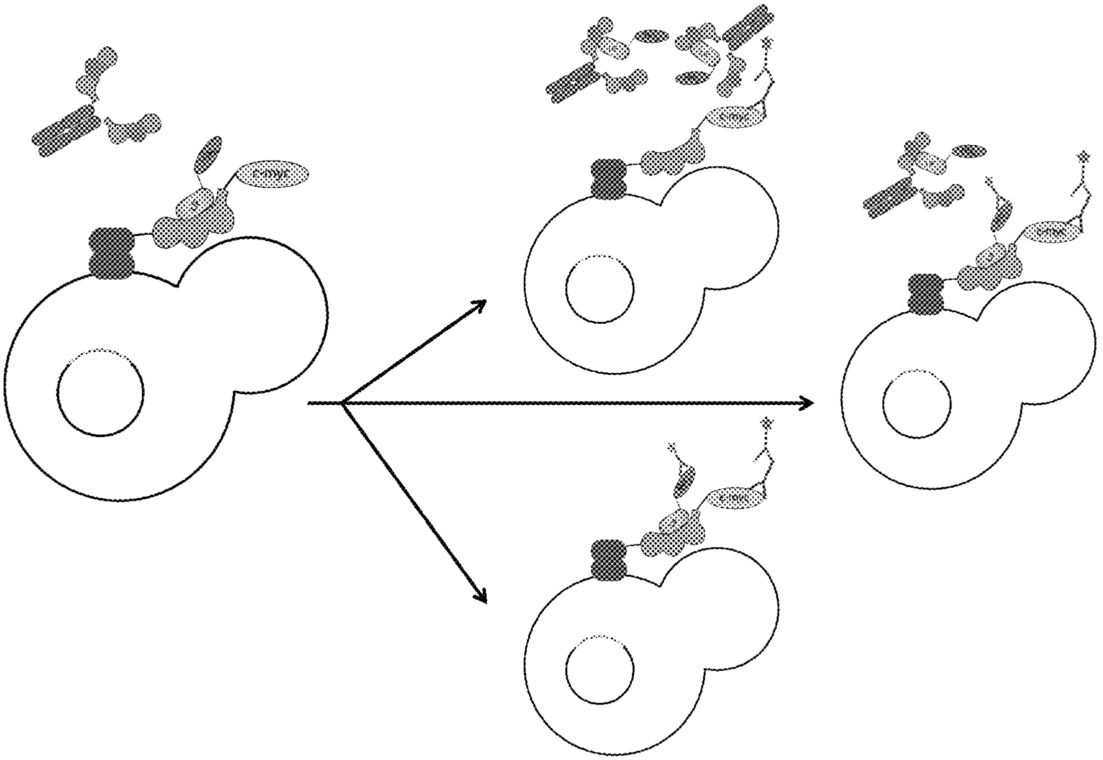
Figure 14:
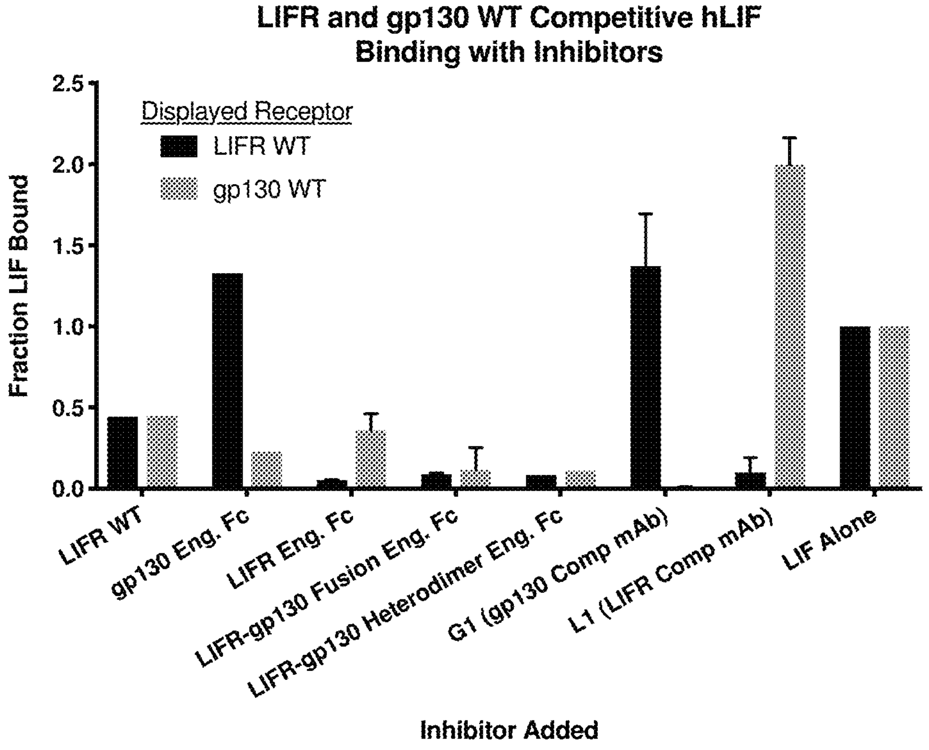

FIG. 14 LIF inhibitors compete LIF away from wild-type receptors. Panel A: Schematic illustration of competitive binding assay. Wild-type gp130 or LIFR (depicted) are displayed on the surface of yeast. Human LIF-His is incubated at saturating concentrations. Inhibitors (LIFR-VPRVVAID-Fc depicted) are then co-incubated with LIF-bound yeast, in excess. LIF binding is detected via His6-tag on LIF. The less LIF that remains bound after inhibitor incubation, the better the inhibitor is able to compete LIF away from the WT receptor. Panel B: Results from competitive binding experiment. Either wild-type LIFR or gp130 were displayed on yeast and saturated with human LIF-His. Fraction bound is the fluorescent emission detected from the LIF-His, normalized to No Inhibitor added. Competitive binding of LIFR-WT-Fc, gp130-ELDME-Fc (Eng.), LIFR-VPRVVAID-Fc (Eng.), LIFR-gp130 Fusion-Fc (Eng.), LIFR-gp130 Heterodimeric Fc (Eng.), Anti-LIF mAb L1, and Anti-LIF mAb G1 are shown.

Figure 15:
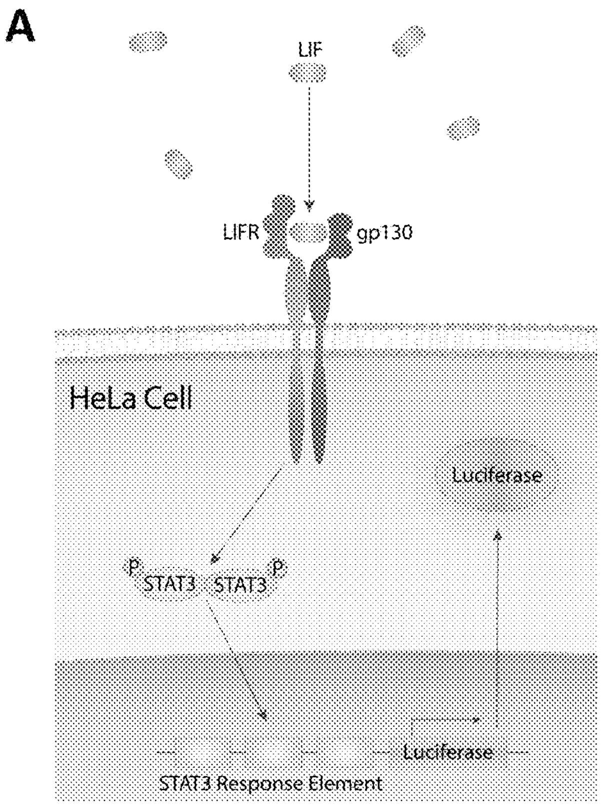
Figure 15:
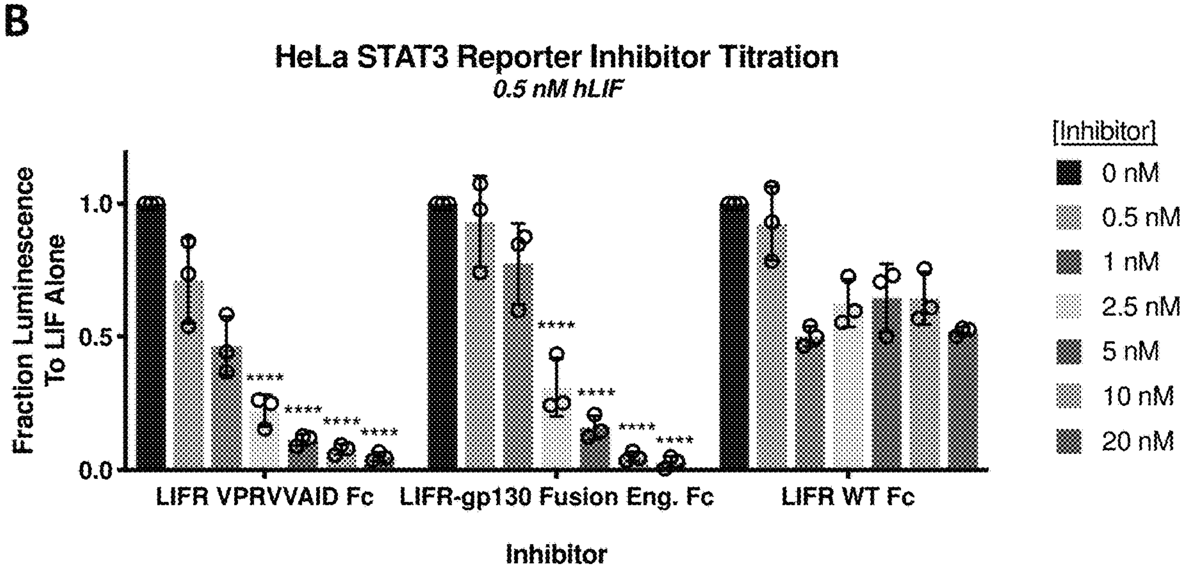
Figure 15:
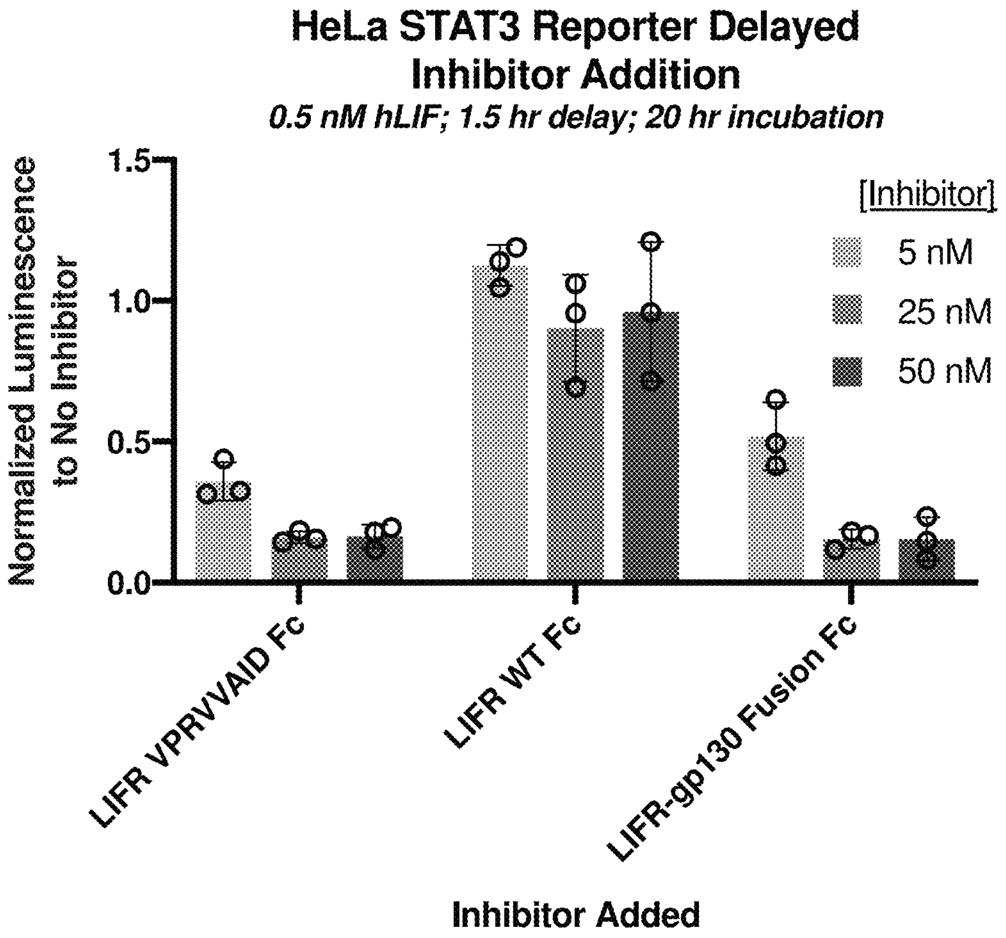
Figure 15:
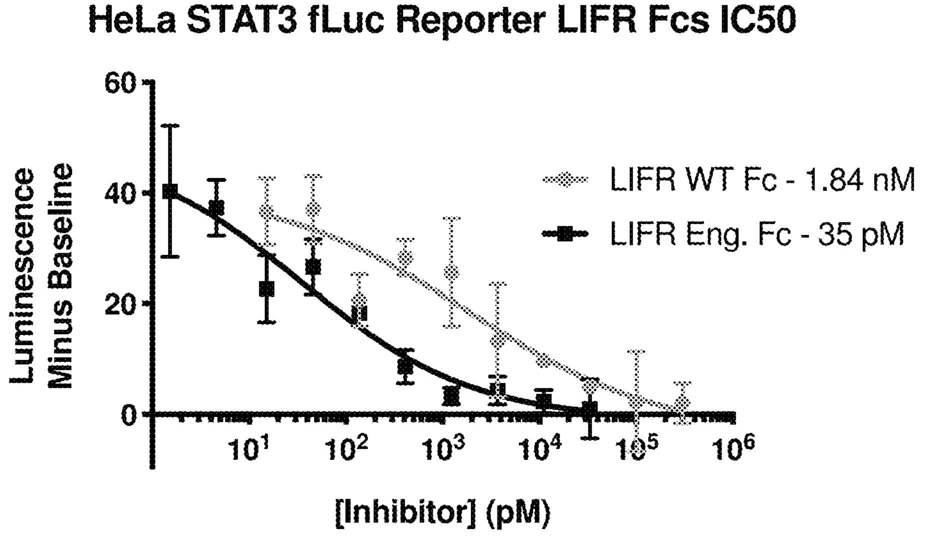
Figure 15:
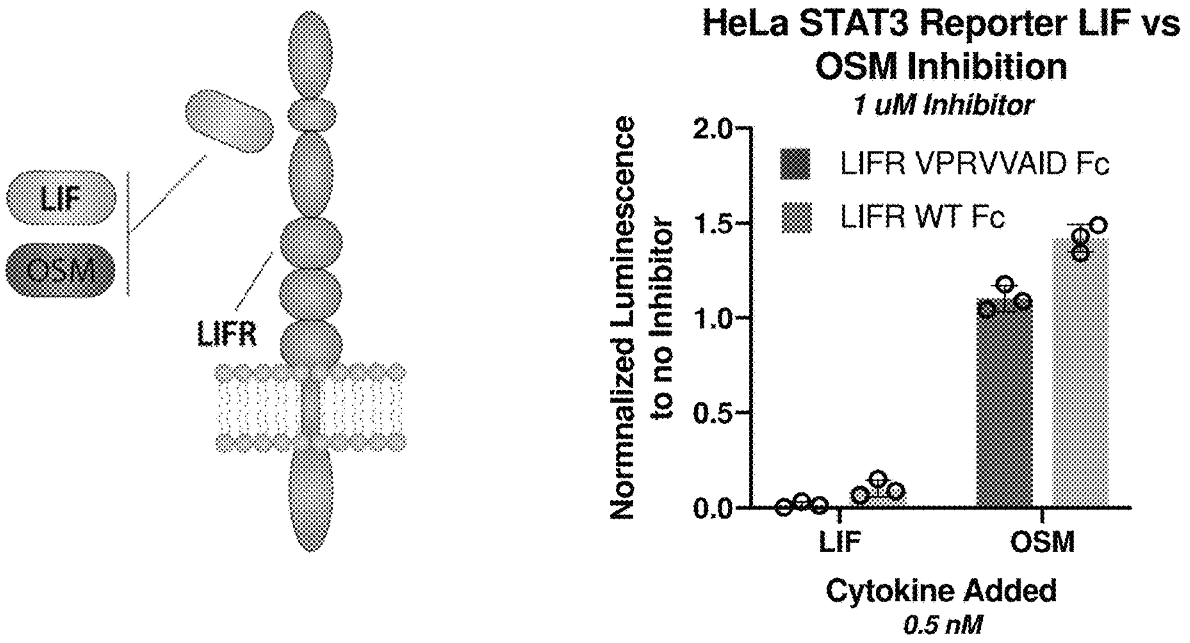

FIG. 15 Engineered inhibitors block downstream STAT3 signaling in HeLa luciferase reporter cells. Panel A: Schematic of LIF signaling in HeLa reporter cells. LIF promotes the dimerization of LIFR and gp130, leading to STAT3 phosphorylation, activation of downstream signaling, and ultimately production of luciferase under control of a STAT3 response element. Panel B: Inhibition of LIF derived luciferase activity by varying concentrations of LIFR VPRVVAID Fc, LIFR-gp130 Fusion Engineered Fc, and LIFR WT Fc. Panel C: LIF derived luciferase signal upon delayed addition of LIFR Fc or Fusion Fc. Panel D: Inhibition of LIF derived luciferase activity over many orders of magnitude of [inhibitor]. LIFR VPRVVAID Fc IC50=35 pM, 53× improvement over LIFR WT Fc. Panel E: Cartoon—IL-6 family members LIF and OSM binding LIFR. Graph—Measure of luciferase signal derived from LIF or OSM, incubated with LIFR VPRVVAID Fc or LIFR WT Fc.

Figure 16:
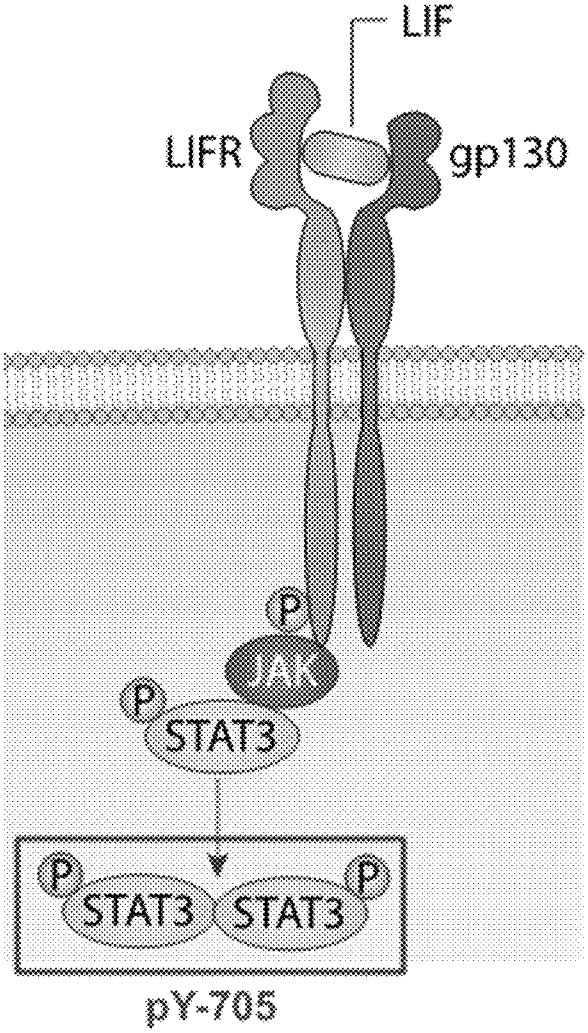
Figure 16:
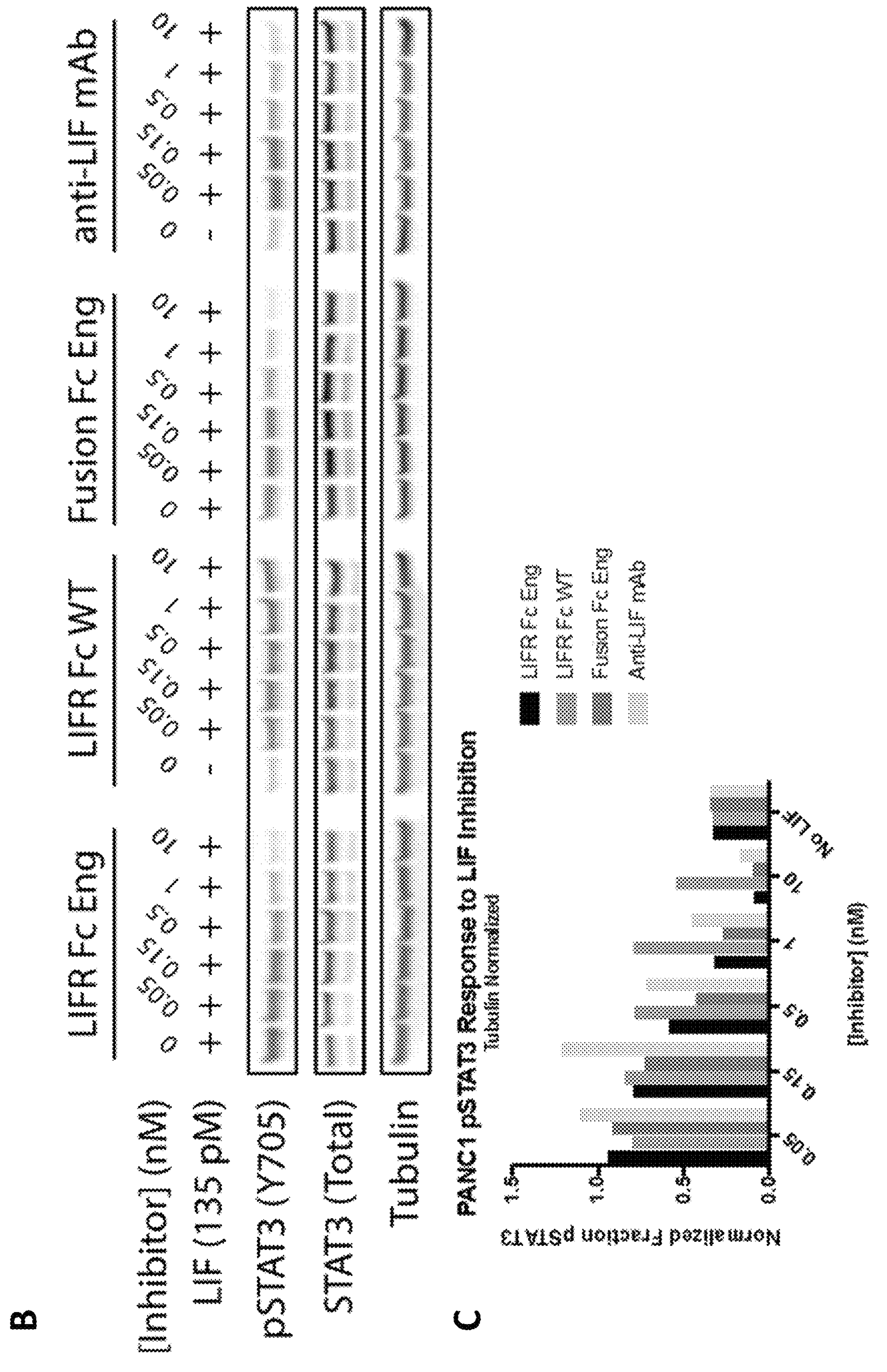

FIG. 16 LIF Inhibitors ablate LIF signaling in pancreatic cancer cells. Panel A: Schematic illustration of LIF signaling. LIF binds to LIFR and gp130, causing hetero-dimerization of receptors. Dimerization results in recruitment of JAK, which phosphorylates STAT3 on tyrosine 705. This results in STAT3 dimerization, nuclear entry, and activation of transcriptional programming. Thus, pSTAT3-Y705 is a read-out of LIF signaling. Panel B: Western blot of PANC1 (human pancreatic cancer cell line) lysates exposed to 135 pM human LIF and differing concentrations of LIFR-VPRVVAID-Fc (Eng.), LIFR-WT-Fc, LIFR-VPRVVAID-gp130-ELDME Fc, and L1 Anti-LIF mAb. Panel C: Quantification of pSTAT3 signal, normalized to tubulin signal.

DETAILED DESCRIPTION

Provided are soluble leukemia inhibitory factor receptor (LIFR) polypeptides, soluble glycoprotein 130 (gp130) polypeptides, and soluble fusion proteins and dimers including such polypeptides. The soluble polypeptides bind to leukemia inhibitory factor (LIF). In certain aspects, the soluble polypeptides exhibit increased binding affinity for LIF relative to the corresponding wild-type polypeptides. Also provided are nucleic acids encoding such soluble polypeptides, expression vectors including such nucleic acids, and cells including such nucleic acids and/or expression vectors. Methods of using the soluble polypeptides, including methods of inhibiting LIF activity in an individual in need thereof (e.g., to treat cancer), are also provided.

Before the soluble polypeptides, nucleic acids, expression vectors, cells and methods of the present disclosure are described in greater detail, it is to be understood that the soluble polypeptides, nucleic acids, expression vectors, cells and methods are not limited to particular embodiments described, as such may, of course, vary. It is also to be understood that the terminology used herein is for the purpose of describing particular embodiments only, and is not intended to be limiting, since the scope of the soluble polypeptides, nucleic acids, expression vectors, cells and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the soluble polypeptides, nucleic acids, expression vectors, cells and methods. The upper and lower limits of these smaller ranges may independently be included in the smaller ranges and are also encompassed within the soluble polypeptides, nucleic acids, expression vectors, cells and methods, subject to any specifically excluded limit in the stated range. Where the stated range includes one or both of the limits, ranges excluding either or both of those included limits are also included in the soluble polypeptides, nucleic acids, expression vectors, cells and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the soluble polypeptides, nucleic acids, expression vectors, cells and methods belong. Although any soluble polypeptides, nucleic acids, expression vectors, cells and methods similar or equivalent to those described herein can also be used in the practice or testing of the soluble polypeptides, nucleic acids, expression vectors, cells and methods, representative illustrative soluble polypeptides, nucleic acids, expression vectors, cells and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present soluble polypeptides, nucleic acids, expression vectors, cells and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the soluble polypeptides, nucleic acids, expression vectors, cells and methods, which are, for clarity, described in the context of separate embodiments, may also be provided in combination in a single embodiment. Conversely, various features of the soluble polypeptides, nucleic acids, expression vectors, cells and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present soluble polypeptides, nucleic acids, expression vectors, cells and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Soluble Polypeptides

As summarized above, aspects of the present disclosure include soluble polypeptides. The soluble polypeptides bind to leukemia inhibitory factor (LIF) (UniProtKB—P15018 (human) and UniProtKB—P09056 (mouse)) and inhibit LIF activity. LIF is a multi-functional cytokine and its receptors include leukemia inhibitory factor receptor (LIFR) (UniProtKB—P42702 (human) and UniProtKB—P42703 (mouse)) and glycoprotein 130 (gp130) (UniProtKB—P40189 (human) and UniProtKB—Q00560 (mouse)).

Figure 1:
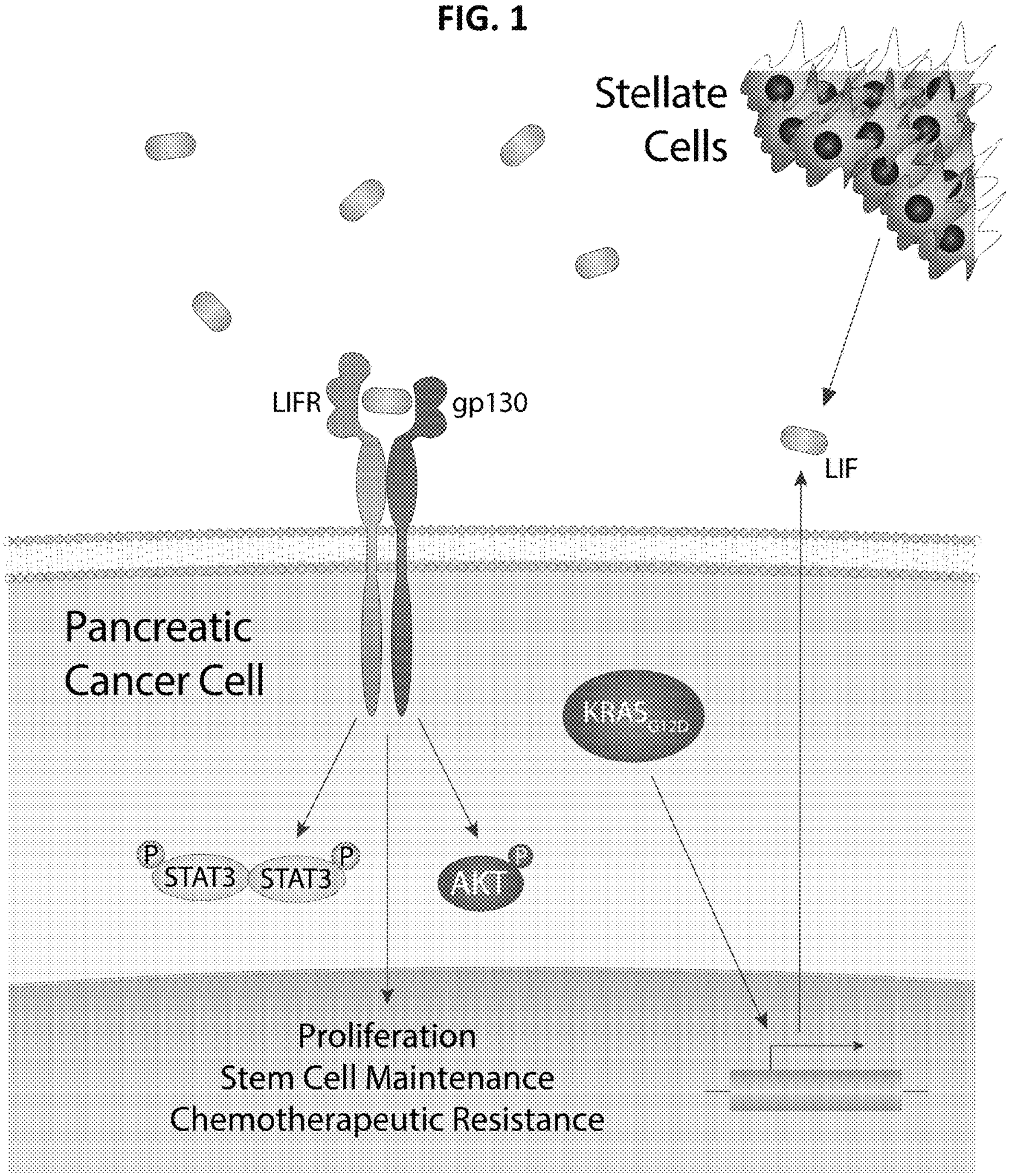
FIG. 1 Schematic illustration of LIF signaling through LIFR and gp130.

As schematically illustrated in FIG. 1, FIG. 15, panel A, and FIG. 16, panel A, LIF binds to LIFR and gp130, causing hetero-dimerization of the receptors. Dimerization results in recruitment of JAK, which phosphorylates STAT3 on tyrosine 705. This results in STAT3 dimerization, nuclear entry, and activation of transcriptional programming.

Figure 2:
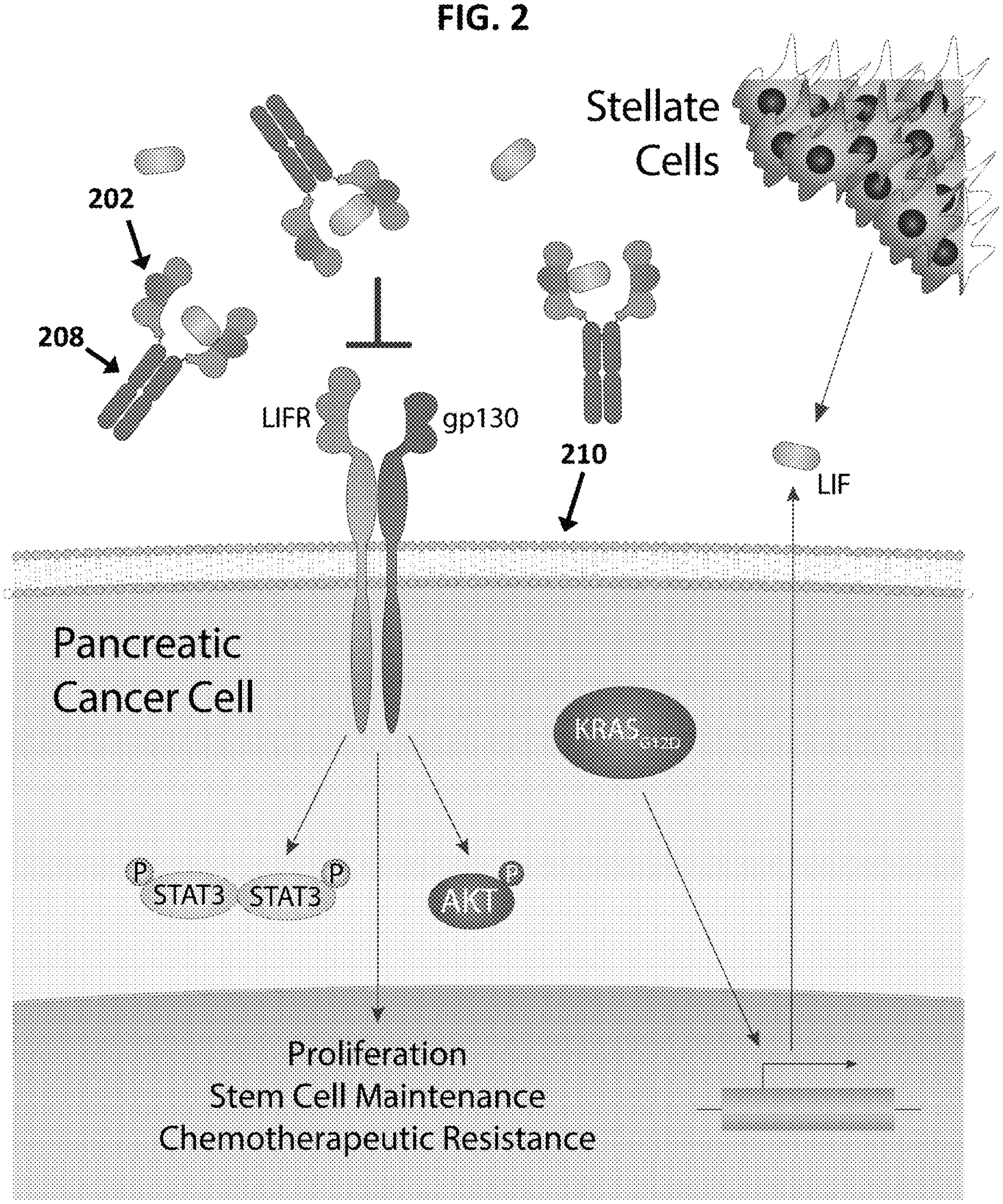
FIG. 2 Schematic illustration of inhibition of LIF activity using a dimer of soluble polypeptides according to one embodiment of the present disclosure.

The present polypeptides are based on extracellular (and hence, soluble) portions of LIFR and/or gp130 and find use in a variety of contexts. For example, the soluble polypeptides find use as a therapeutic when administered to an individual in need thereof, e.g., an individual having a cancer or other medical condition for which inhibition of LIF activity would be beneficial. The soluble polypeptides may be used as "decoy" receptors which act as a LIF ligand "trap" so that the availability of LIF for binding to its native receptors on the surface of cells (e.g., cancer cells) is substantially reduced or eliminated—thereby reducing or eliminating LIF activity/signaling. A schematic illustration of such a LIF ligand trap according to one embodiment is schematically illustrated in FIG. 2. In this example, the soluble polypeptides are dimerized, where each monomer of the dimer includes LIFR portion 202 (here, a portion that includes the first three domains of human LIFR (cytokine binding motif I—Ig-like—cytokine binding motif II)) fused (directly or indirectly) to fragment crystallizable (Fc) domain 208 (e.g., a human IgG1 Fc domain, a mouse IgG2a Fc domain, or the like). As illustrated in FIG. 2, the dimers act as a LIF ligand trap that sequesters LIF from its native LIFR and gp130 receptors on the surface of cell 210, thereby inhibiting LIF signaling/activity. The soluble polypeptides of the present disclosure also find use in diagnostic applications, e.g., for detecting LIF as a biomarker for cancer (e.g., pancreatic cancer) detection, and also in research applications, e.g., for inhibiting LIF signaling/activity to determine the biological effects of LIF. The soluble polypeptides of the present disclosure will now be described in further detail.

Soluble LIFR Polypeptides

The present disclosure provides soluble LIFR polypeptides. By "soluble LIFR polypeptide" is meant a LIFR polypeptide that is not integrated into a cell membrane, e.g., because the soluble LIFR polypeptide only includes the extracellular portion of LIFR or a fragment thereof. In some embodiments, the soluble LIFR polypeptide includes, consists essentially of, or consists of, the first three domains of LIFR, which are, in an N-to C-terminal order: (1) the cytokine binding motif I (CBMI) domain; (2) the Ig-like domain; and (3) the cytokine binding motif II (CBMII) domain. Shown in Table 1 below is the amino acid sequence of wild-type human LIFR (excluding the signal sequence). The underlined amino acids make up the CBMI, Ig-like, and CBMII domains.

TABLE 1

| Wild-type human LIFR amino acid sequence | |
|---|---|
| Wild-Type Human LIFR Amino Acid Sequence (SEQ ID NO: 1) Underlined: CBMI-CBMII (SEQ ID NO: 2) | QKKGAPHDLKCVTNNLQVWNCSWKAPSGTG<br>RGTDYEVCIENRSRSCYQLEKTSIKIPALS<br>HGDYEITINSLHDFGSSTSKFTLNEQNVSL<br>IPDTPEILNLSADFSTSTLYLKWNDRGSVF<br>PHRSNVIWEIKVLRKESMELVKLVTHNTTL<br>NGKDTLHHWSWASDMPLECAIHFVEIRCYI<br>DNLHFSGLEEWSDWSPVKNISWIPDSQTKV<br>FPQDKVILVGSDITFCCVSQEKVLSALIGH<br>TNCPLIHLDGENVAIKIRNISVSASSGTNV<br>VFTTEDNIFGTVIFAGYPPDTPQQLNCETH<br>DLKEIICSWNPGRVTALVGPRATSYTLVES<br>FSGKYVRLKRAEAPTNESYQLLFQMLPNQE<br>IYNFTLNAHNPLGRSQSTILVNITEKVYPH<br>TPTSFKVKDINSTAVKLSWHLPGNFAKINF<br>LCEIEIKKSNSVQEQRNVTIKGVENSSYLV<br>ALDKLNPYTLYTFRIRCSTETFWKWSKWSN<br>KKQHLTTEASPSKGPDTWREWSSDGKNLII<br>YWKPLPINEANGKILSYNVSCSSDEETQSL<br>SEIPDPQHKAEIRLDKNDYIISVVAKNSVG<br>SSPPSKIASMEIPNDDLKIEQVVGMGKGIL<br>LTWHYDPNMTCDYVIKWCNSSRSEPCLMDW<br>RKVPSNSTETVIESDEFRPGIRYNFFLYGC<br>RNQGYQLLRSMIGYIEELAPIVAPNFTVED<br>TSADSILVKWEDIPVEELRGFLRGYLFYFG<br>KGERDTSKMRVLESGRSDIKVKNITDISQK<br>TLRIADLQGKTSYHLVLRAYTDGGVGPEKS<br>MYVVTKENS |

In certain aspects, a soluble LIFR polypeptide of the present disclosure includes an amino acid sequence that is at least 70%, at least 75%, at least 80%, at least 85%, at least 90%, at least 95%, at least 99%, or 100% identical to SEQ ID NO:2, or a LIF-binding fragment thereof that includes from 400 to 489, 420 to 489, 440 to 489, 460 to 489, 470 to 489, 475 to 489, 480 to 489, or 485 to 489 contiguous amino acids of the amino acid sequence set forth in SEQ ID NO:2.

A soluble LIFR polypeptide may have a wild-type LIFR amino acid sequence. In other aspects, a soluble LIFR polypeptide is a "variant" which contains one or more conservative amino acid substitutions, one or more amino acid substitutions which increase the binding affinity for LIF relative to a corresponding wild-type LIFR polypeptide (e.g., one or more of any of the amino acid substitutions described herein which increase the binding affinity of LIFR for LIF), or a combination thereof. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence.

As summarized above, a soluble LIFR polypeptide of the present disclosure may include an amino acid sequence that is at least 70% identical to SEQ ID NO:2, where the LIFR polypeptide exhibits increased binding affinity for LIF relative to a corresponding wild-type LIFR polypeptide. As used herein, a "corresponding" wild-type polypeptide is the parental wild-type polypeptide (from human, mouse, or the like) which was engineered to include one or more affinity-increasing amino acid substitutions.

As used herein, "increased binding affinity" means that the soluble LIFR polypeptide or soluble gp130 polypeptide exhibits tighter binding (as indicated by a lower $K_D$ value) to LIF as compared to the corresponding wild-type polypeptide. Methods are available for measuring the binding affinity of a soluble LIFR or gp130 polypeptide for LIF. For example, surface plasmon resonance (SPR) technology (e.g., using a BIAcore™ 2000 instrument), KinExA® kinetic exclusion assay (Sapidyne Instruments), Bio-Layer Interferometry (BLI) technology (e.g., ForteBio Octet®), or other similar assay/technology may be employed to determine whether a soluble LIFR or gp130 polypeptide exhibits a desired binding affinity. Suitable approaches for measuring binding affinity in the context of the present disclosure include, e.g., those described in Hunter, S. A. and Cochran, J. R. (2016) *Methods Enzymol.* 580:21-44.

In some embodiments, in a direct binding assay, an equilibrium binding constant ($K_D$) may be measured using a soluble LIFR or gp130 polypeptide conjugated to a fluorophore or radioisotope, or a soluble LIFR or gp130 polypeptide that contains an N- or C-terminal epitope tag for detection by a labeled antibody. If labels or tags are not feasible or desired, a competition binding assay can be used to determine the half-maximal inhibitory concentration ($IC_{50}$), the amount of unlabeled soluble LIFR or gp130 polypeptide at which 50% of the maximal signal of the labeled competitor is detectable. A $K_D$ value can then be calculated from the measured $IC_{50}$ value.

In certain aspects, a soluble LIFR polypeptide having increased binding affinity for LIF includes one or both of: an amino acid substitution at position L218, and an amino acid substitution at position N277, where identification of positions is relative to SEQ ID NO:2. Non-limiting examples of amino acid substitutions at positions L218 and N277 include one or both of a L218P amino acid substitution, and a N277D amino acid substitution.

In some embodiments, a soluble LIFR polypeptide having increased binding affinity for LIF includes one, two, or each of: an amino acid substitution at position 1257, an amino acid substitution at position V262, and an amino acid substitution at position T273, where identification of positions is relative to SEQ ID NO:2. Examples of amino acid substitutions at positions 1257, V262, and T273 include, but are not limited to, one, two, or each of: a I257V amino acid substitution, a V262A amino acid substitution, and a T273I amino acid substitution.

In certain aspects, a soluble LIFR polypeptide having increased binding affinity for LIF includes one, two, or each of: an amino acid substitution at position 1217, an amino acid substitution at position H240, and an amino acid substitution at position 1260, where identification of positions is relative to SEQ ID NO:2. Non-limiting examples of amino acid substitutions at positions 1217, H240, and 1260 include one, two, or each of: a I217V amino acid substitution, a H240R amino acid substitution, and a I260V amino acid substitution.

In some embodiments, a soluble LIFR polypeptide having increased binding affinity for LIF includes an amino acid substitution at position N242, where identification of the position is relative to SEQ ID NO:2. A non-limiting example of a N242 amino acid substitution is a N242D amino acid substitution.

In certain aspects, a soluble LIFR polypeptide of the present disclosure includes an amino acid sequence that is at least 70%, at least 75%, at least 80%, at least 85%, at least 90%, at least 95%, or at least 98% identical to SEQ ID NO:2, or a LIF-binding fragment thereof that includes from 400 to 489, 420 to 489, 440 to 489, 460 to 489, 470 to 489, 475 to 489, 480 to 489, or 485 to 489 contiguous amino acids of the amino acid sequence set forth in SEQ ID NO:2, where the soluble LIFR polypeptide includes one or more amino acid substitutions at any of positions 1217, L218, H240, 1257, 1206, V262, T273, and N277, in any combination.

In some embodiments, a soluble LIFR polypeptide of the present disclosure includes an amino acid sequence that is at least 70%, at least 75%, at least 80%, at least 85%, at least 90%, at least 95%, or at least 98% identical to SEQ ID NO:2, or a LIF-binding fragment thereof that includes from 400 to 489, 420 to 489, 440 to 489, 460 to 489, 470 to 489, 475 to 489, 480 to 489, or 485 to 489 contiguous amino acids of the amino acid sequence set forth in SEQ ID NO:2, where the soluble LIFR polypeptide includes one or more of any of the amino acid substitutions described herein which increase the binding affinity of LIFR for LIF, e.g., one, two, three, four, five, six, seven or each of the amino acid substitutions I217V, L218P, H240R, I257V, I206V, V262A, T273I, and N277D, as described elsewhere herein, in any combination.

Soluble gp130 Polypeptides

Also provided by the present disclosure are soluble gp130 polypeptides. By "soluble gp130 polypeptide" is meant a gp130 polypeptide that is not integrated into a cell membrane, e.g., because the soluble gp130 polypeptide only includes the extracellular portion of gp130 or a fragment thereof. In some embodiments, the soluble gp130 polypeptide includes, consists essentially of, or consists of, the cytokine binding motif (CBM) domain of gp130. Shown in Table 2 below is the amino acid sequence of wild-type human gp130 (excluding the signal sequence). The underlined amino acids make up the CBM domain.

TABLE 2

| Wild-type human gp130 amino acid sequence | |
|---|---|
| Wild-Type Human gp130 Amino Acid Sequence (SEQ ID NO: 3) Underlined: CBM (SEQ ID NO: 4) | ELLDPCGYISPESPVVQLHSNFTAVCVLKE<br>KCMDYFHVNANYIVWKTNHFTIPKEQYTII<br>NRTASSVTFTDIASLNIQLTCNILTFGQLE<br>QNVYGITIISGLPPEKPKNLSCIVNEGKKM<br>RCEWDRGRETHLETNFTLKSEWATHKFADC<br>KAKRDTPTSCTVDYSTVYFVNIEVWVEAEN<br>ALGKVTSDHINFDPVYKVKPNPPHNLSVIN<br>SEELSSILKLTWTNPSIKSVIILKYNIQYR<br>TKDASTWSQIPPEDTASTRSSFTVQDLKPF<br>TEYVFRIRCMKEDGKGYWSDWSEEASGITY |

TABLE 2-continued

| Wild-type human gp130 amino acid sequence | |
|---|---|
| | EDRPSKAPSFWYKIDPSHTQGYRTVQLVWK<br>TLPPFEANGKILDYEVTLTRWKSHLQNYTV<br>NATKLTVNLTNDRYVATLTVRNLVGKSDAA<br>VLTIPACDFQATHPVMDLKAFPKDNMLWVE<br>WTTPRESVKKYILEWCVLSDKAPCITDWQQ<br>EDGTVHRTYLRGNLAESKCYLITVTPVYAD<br>GPGSPESIKAYLKQAPPSKGPTVRTKKVGK<br>NEAVLEWDQLPVDVQNGFIRNYTIFYRTII<br>GNETAVNVDSSHTEYTLSSLTSDTLYMVRM<br>AAYTDEGGKDGPEFTFTTPKFAQGEIE |

In certain aspects, a soluble gp130 polypeptide of the present disclosure includes an amino acid sequence that is at least 70%, at least 75%, at least 80%, at least 85%, at least 90%, at least 95%, at least 99%, or 100% identical to SEQ ID NO:4, or a LIF-binding fragment thereof that includes from 150 to 200, 160 to 200, 170 to 200, 180 to 200, 185 to 200, 190 to 200, or 195 to 200 contiguous amino acids of the amino acid sequence set forth in SEQ ID NO:4.

A soluble gp130 polypeptide may have a wild-type gp130 amino acid sequence. In other aspects, a soluble gp130 polypeptide is a "variant" which contains one or more conservative amino acid substitutions, one or more amino acid substitutions which increase the binding affinity for LIF relative to a corresponding wild-type gp130 polypeptide (e.g., one or more of any of the amino acid substitutions described herein which increase the binding affinity of gp130 for LIF), or a combination thereof.

As summarized above, a soluble gp130 polypeptide of the present disclosure may include an amino acid sequence that is at least 70% identical to SEQ ID NO:4, where the gp130 polypeptide exhibits increased binding affinity for LIF relative to a corresponding wild-type gp130 polypeptide.

In some embodiments, a soluble gp130 polypeptide having increased binding affinity for LIF includes an amino acid substitution at position K45, where identification of the position is relative to SEQ ID NO:4. A non-limiting example of an amino acid substitution at position K45 is a K45E amino acid substitution.

In certain aspects, a soluble gp130 polypeptide having increased binding affinity for LIF includes one or both of: an amino acid substitution at position Y95, and an amino acid substitution at position K184, where identification of positions is relative to SEQ ID NO:4. Non-limiting examples of amino acid substitutions at positions Y95 and K184 include one or both of: a Y95D amino acid substitution, and a K184E amino acid substitution.

In some embodiments, a soluble gp130 polypeptide having increased binding affinity for LIF includes one or both of: an amino acid substitution at position F46, and an amino acid substitution at position 1130, where identification of positions is relative to SEQ ID NO:4. Examples of amino acid substitutions at positions F46 and 1130 include, but are not limited to, one or both of: a F46L amino acid substitution, and a I130M amino acid substitution.

In certain aspects, a soluble gp130 polypeptide of the present disclosure includes an amino acid sequence that is at least 70%, at least 75%, at least 80%, at least 85%, at least 90%, at least 95%, or at least 98% identical to SEQ ID NO:4, or a LIF-binding fragment thereof that includes from 150 to 200, 160 to 200, 170 to 200, 180 to 200, 185 to 200, 190 to 200, or 195 to 200 contiguous amino acids of the amino acid sequence set forth in SEQ ID NO:4, where the soluble gp130 polypeptide includes one or more amino acid substitutions at any of positions K45, F46, Y95, 1130, and K184, in any combination.

le;.4qIn some embodiments, a soluble gp130 polypeptide of the present disclosure includes an amino acid sequence that is at least 70%, at least 75%, at least 80%, at least 85%, at least 90%, at least 95%, or at least 98% identical to SEQ ID NO:4, or a LIF-binding fragment thereof that includes from 150 to 200, 160 to 200, 170 to 200, 180 to 200, 185 to 200, 190 to 200, or 195 to 200 contiguous amino acids of the amino acid sequence set forth in SEQ ID NO:4, where the soluble gp130 polypeptide includes one or more of any of the amino acid substitutions described herein which increase the binding affinity of gp130 for LIF, e.g., one, two, three, four or each of the amino acid substitutions K45E, F46L, Y95D, I130M, and K184E, as described elsewhere herein, in any combination.

le;.4qFusion and Dimeric Proteins le;.4qAlso provided are fusion proteins that include any of the soluble LIFR polypeptides or soluble gp130 polypeptides of the present disclosure. By "fusion protein" is meant a fusion that includes a soluble LIFR polypeptide or soluble gp130 polypeptide fused to one or more heterologous polypeptides as part of a single continuous chain of amino acids, which chain does not occur in nature. In certain aspects, the one or more heterologous polypeptides is selected from an Fc domain, an albumin, a transferrin, XTEN, a homo-amino acid polymer, a proline-alanine-serine polymer, an elastin-like peptide, and any combination thereof. In certain aspects, a fusion protein includes a soluble LIFR polypeptide fused to a soluble gp130 polypeptide.

le;.4qTwo or more domains of the fusion proteins of the present disclosure may be fused directly or indirectly. For example, a soluble LIFR polypeptide may be fused to a soluble gp130 polypeptide indirectly via a linker. Also by way of example, a soluble LIFR polypeptide or soluble gp130 polypeptide may be fused to a heterologous peptide (e.g., an Fc domain) via a linker. Suitable linkers include, but are not limited to, peptide linkers. In certain aspects, a peptide linker is a linker comprising glycine and serine, e.g., a GlySer linker. GlySer linkers of interest include, but are not limited to, $(Gly4Ser)_n$ linkers.

le;.4qIn some embodiments, the one or more heterologous polypeptides comprises an Fc domain, e.g., a human Fc domain or a mouse Fc domain. The Fc domain may be a full-length Fc domain or a fragment thereof. A non-limiting example of a human Fc domain that may be fused to any of the soluble LIFR or gp130 polypeptides of the present disclosure is a human IgG1 Fc domain having the sequence set forth in Table 3 below (SEQ ID NO:5), or a fragment thereof.

TABLE 3

| Human IgG1 Fc domain amino acid sequence | |
|---|---|
| Human IgG1 Fc domain amino acid sequence (SEQ ID NO: 5) | DKTHTCPPCPAPELLGGPSVFLFPPKPKDTL<br>MISRTPEVTCVVVDVSHEDPEVKFNWYVDGV<br>EVHNAKTKPREEQYNSTYRVVSVLTVLHQDW<br>LNGKEYKCKVSNKALPAPIEKTISKAKGQPR<br>EPQVYTLPPSRDELTKNQVSLTCLVKGFYPS<br>DIAVEWESNGQPENNYKTTPPVLDSDGSFFL<br>YSKLTVDKSRWQQGNVFSCSVMHEALHNHYT<br>QKSLSLSPGK |

TABLE 3-continued

Provided in Table 4 are amino acid sequences of example fusion proteins of the present disclosure (signal sequences excluded). Provided is an amino acid sequence of a fusion protein ("gp130 ELDME hIgG1") that includes a gp130 domain (underlined) fused to a human IgG1 Fc domain (italicized) via a linker (here, a 3× glycine-serine (GS) linker; wavy underlined)) (SEQ ID NO: 6). The gp130 domain includes the amino acid substitutions K45E, F46L, Y95D, I130M, and K184E ("ELDME") as described elsewhere herein. This fusion protein corresponds to the monomers of the dimeric protein schematically illustrated in FIG. 9, panel C. Also provided in Table 4 is an amino acid sequence of a fusion protein ("LIFR VPRVVAID hIgG1") that includes a LIFR Cytokine Binding Motif I (CBMI)—Cytokine Binding Motif II (CBMII) domain (underlined) fused to a human IgG1 Fc domain (italicized) via a linker (here, a 3× glycine-serine (GS) linker; wavy underlined) (SEQ ID NO:7). The LIFR Cytokine Binding Motif I (CBMI)—Cytokine Binding Motif II (CBMII) domain includes the amino acid substitutions I217V, L218P, H240R, I257V, I206V, V262A, T273I, and N277D ("VPRVVAID") as described elsewhere herein. This fusion protein corresponds to the monomers of the dimeric protein schematically illustrated in FIG. 9, panel D. Table 4 also provides an amino acid sequence of a fusion protein ("LIFR-gp130 VPRVVAID-ELDME hIgG1") that includes the VPRVVAID LIFR domain (underlined) of the "LIFR VPRVVAID hIgG1" fusion protein fused to the ELDME gp130 domain (double underlined) of the "gp130 ELDME hIgG1" fusion protein via a linker (here, a 5× $glycine_4$-$serine_1$ (G45) linker; dashed underline), where the ELDME gp130 domain is fused to a human IgG1 Fc domain (italicized) via a linker (here, a 3× glycine-serine (GS) linker; wavy underlined) (SEQ ID NO:8). This fusion protein corresponds to the monomers of the dimeric protein schematically illustrated in FIG. 9, panel E. Table 4 further provides amino acid sequences of the fusion protein monomers of the dimeric protein schematically illustrated in FIG. 9, panel F. The first monomer includes the VPRVVAID LIFR domain (underlined) of the "LIFR VPRVVAID hIgG1" fusion protein fused to a human IgG1 Fc knobs-in-holes (KiH) CH3A domain (italicized) via a linker (here, a 3× glycine-serine (GS) linker; wavy underlined) (SEQ ID NO:9). The second monomer includes the ELDME gp130 domain (underlined) of the "gp130 ELDME hIgG1" fusion protein fused to a human IgG1 Fc knobs-in-holes (KiH) CH3B domain (italicized) via a linker (here, a 3× glycine-serine (GS) linker; wavy underlined) (SEQ ID NO:10).

TABLE 4

| Amino acid sequences of example fusion proteins | |
|---|---|
| gp130 ELDME hIgG1 amino acid sequence (SEQ ID NO: 6) | LPPEKPKNLSCIVNEGKKMRCEWDRGRETHLETNFTLKSEWA<br>THELADCKAKRDTPTSCTVDYSTVYFVNIEVWVEAENALGKV<br>TSDHINFDPVDKVKPNPPHNLSVINSEELSSILKLTWTNPSIKS<br>VMILKYNIQYRTKDASTWSQIPPEDTASTRSSFTVQDLKPFTE<br>YVFRIRCMKEDGEGYWSDWSEEASGITYEDGSGSGS*DKTHT*<br>*CPPCPAPELLGGPSVFLFPPKPKDTLMISRTPEVTCVVVDVSH* |

TABLE 4-continued

| Amino acid sequences of example fusion proteins | |
|---|---|
| | *EDPQVKFNWYVDGVQVHNAKTKPREQQYNSTYRVVSVLTVL HQNWLDGKEYKCKVSNKALPAPIEKTISKAKGQPREPQVYTL PPSREEMTKNQVSLTCLVKGFYPSDIAVEWESNGQPENNYK TTPPVLDSDGSFFLYSKLTVDKSRWQQGNVFSCSVMHEALH NHYTQKSLSLSPGK* |
| LIFR VPRVVAID hIgG1 amino acid sequence (SEQ ID NO: 7) | QKKGAPHDLKCVTNNLQVWNCSWKAPSGTGRGTDYEVCIEN RSRSCYQLEKTSIKIPALSHGDYEITINSLHDFGSSTSKFTLNE QNVSLIPDTPEILNLSADFSTSTLYLKWNDRGSVFPHRSNVIW EIKVLRKESMELVKLVTHNTTLNGKDTLHHWSWASDMPLECA IHFVEIRCYIDNLHFSGLEEWSDWSPVKNISWIPDSQTKVFPQ DKVVPVGSDITFCCVSQEKVLSALIGRTDCPLIHLDGENVAIKV RNVSASASSGTNVVFITEDDIFGTVIFAGYPPDTPQGSQLNCE THDLKEIICSWNPGRVTALVGPRATSYTLVESFSGKYVRLKRA EAPTNESYQLLFQMLPNQEIYNFTLNAHNPLGRSQSTILVNITE KVYPHTPTSFKVKDINSTAVKLSWHLPGNFAKINFLCEIEIKKS NSVQEQRNVTIKGVENSSYLVALDKLNPYTLYTFRIRCSTETF WKWSKWSNKKQHLTTEASGSGSGS*DKTHTCPPCPAPELLG GPSVFLFPPKPKDTLMISRTPEVTCVVVDVSHEDPQVKFNWY VDGVQVHNAKTKPREQQYNSTYRVVSVLTVLHQNWLDGKEY KCKVSNKALPAPIEKTISKAKGQPREPQVYTLPPSREEMTKNQ VSLTCLVKGFYPSDIAVEWESNGQPENNYKTTPPVLDSDGSF FLYSKLTVDKSRWQQGNVFSCSVMHEALHNHYTQKSLSLSP GK* |
| LIFR-gp130 VPRVVAID-ELDME hIgG1 amino acid sequence (SEQ ID NO: 8) | QKKGAPHDLKCVTNNLQVWNCSWKAPSGTGRGTDYEVCIEN RSRSCYQLEKTSIKIPALSHGDYEITINSLHDFGSSTSKFTLNE QNVSLIPDTPEILNLSADFSTSTLYLKWNDRGSVFPHRSNVIW EIKVLRKESMELVKLVTHNTTLNGKDTLHHWSWASDMPLECA IHFVEIRCYIDNLHFSGLEEWSDWSPVKNISWIPDSQTKVFPQ DKVVPVGSDITFCCVSQEKVLSALIGRTNCPLIHLDGENVAIKV RNVSASASSGTNVVFITEDDIFGTVIFAGYPPDTPQQLNCETH DLKEIICSWNPGRVTALVGPRATSYTLVESFSGKYVRLKRAEA PTNESYQLLFQMLPNQEIYNFTLNAHNPLGRSQSTILVNITEKV YPHTPTSFKVKDINSTAVKLSWHLPGNFAKINFLCEIEIKKSNS VQEQRNVTIKGVENSSYLVALDKLNPYTLYTFRIRCSTETFWK WSKWSNKKQHLTTEASGGGGSGGGGSGGGGSGGGGSGG GGSLPPEKPKNLSCIVNEGKKMRCEWDRGRETHLETNFTLKS EWATHELADCKAKRDTPTSCTVDYSTVYFVNIEVWVEAENAL GKVTSDHINFDPVDKVKPNPPHNLSVINSEELSSILKLTWTNP SIKSVMILKYNIQYRTKDASTWSQIPPEDTASTRSSFTVQDLKP FTEYVERIRCMKEDGEGYWSDWSEEASGITYEDGSGSGS*DK THTCPPCPAPELLGGPSVFLFPPKPKDTLMISRTPEVTCVVVD VSHEDPQVKFNWYVDGVQVHNAKTKPREQQYNSTYRVVSVL TVLHQNWLDGKEYKCKVSNKALPAPIEKTISKAKGQPREPQV YTLPPSREEMTKNQVSLTCLVKGFYPSDIAVEWESNGQPENN YKTTPPVLDSDGSFFLYSKLTVDKSRWQQGNVFSCSVMHEA LHNHYTQKSLSLSPGK* |
| LIFR VPRVVAID hIgG1 KiH CH3A amino acid sequence (SEQ ID NO: 9) | QKKGAPHDLKCVTNNLQVWNCSWKAPSGTGRGTDYEVCIEN RSRSCYQLEKTSIKIPALSHGDYEITINSLHDFGSSTSKFTLNE QNVSLIPDTPEILNLSADFSTSTLYLKWNDRGSVFPHRSNVIW EIKVLRKESMELVKLVTHNTTLNGKDTLHHWSWASDMPLECA IHFVEIRCYIDNLHFSGLEEWSDWSPVKNISWIPDSQTKVFPQ DKVVPVGSDITFCCVSQEKVLSALIGRTDCPLIHLDGENVAIKV RNVSASASSGTNVVFITEDDIFGTVIFAGYPPDTPQQLNCETH DLKEIICSWNPGRVTALVGPRATSYTLVESFSGKYVRLKRAEA PTNESYQLLFQMLPNQEIYNFTLNAHNPLGRSQSTILVNITEKV YPHTPTSFKVKDINSTAVKLSWHLPGNFAKINFLCEIEIKKSNS VQEQRNVTIKGVENSSYLVALDKLNPYTLYTFRIRCSTETFWK WSKWSNKKQHLTTEASGSGSGS*DKTHTCPPCPAPELLGGPS VFLFPPKPKDTLMISRTPEVTCVVVDVSHEDPQVKFNWYVDG VQVHNAKTKPREQQYNSTYRVVSVLTVLHQNWLDGKEYKCK VSNKALPAPIEKTISKAKGQPREPQVYTLPPSREEMTKNQVSL WCLVKGFYPSDIAVEWESNGQPENNYKTTPPVLDSDGSFFLY SKLTVDKSRWQQGNVFSCSVMHEALHNHYTQKSLSLSPGK* |
| gp130 ELDME hIgG1 KiH CH3B amino acid sequence (SEQ ID NO: 10) | LPPEKPKNLSCIVNEGKKMRCEWDRGRETHLETNFTLKSEWA THELADCKAKRDTPTSCTVDYSTVYFVNIEVWVEAENALGKV TSDHINFDPVDKVKPNPPHNLSVINSEELSSILKLTWTNPSIKS VMILKYNIQYRTKDASTWSQIPPEDTASTRSSFTVQDLKPFTE YVFRIRCMKEDGEGYWSDWSEEASGITYEDGSGSGS*DKTHT CPPCPAPELLGGPSVFLFPPKPKDTLMISRTPEVTCVVVDVSH EDPQVKFNWYVDGVQVHNAKTKPREQQYNSTYRVVSVLTVL HQNWLDGKEYKCKVSNKALPAPIEKTISKAKGQPREPQVYTL PPSREEMTKNQVSLSCAVKGFYPSDIAVEWESNGQPENNYK* |

TABLE 4-continued

| Amino acid sequences of example fusion proteins |
| --- |
| *TTPPVLDSDGSFFLVSKLTVDKSRWQQGNVFSCSVMHEALH NHYTQKSLSLSPGK* |

Also provided are dimeric proteins that include any of the soluble LIFR polypeptides, soluble gp130 polypeptides, or fusion proteins including same (e.g., any of the fusion proteins in Table 4, or LIF-binding variants thereof), dimerized with any of the soluble LIFR polypeptides, soluble gp130 polypeptides, or fusion proteins including same. In some embodiments, each monomer is a fusion protein that includes an Fc domain, and dimerization of the monomers is via the Fc domain. Example dimeric proteins of the present disclosure include those described in the Experimental section below, and those schematically illustrated in FIG. 9.

Engineering/Development and Production of Soluble LIFR and gp130 Polypeptides

Also provided by the present disclosure are methods of engineering/developing additional soluble LIFR or gp130 polypeptides having one or more desired functionalities. The manner in which the soluble LIFR or gp130 polypeptides are developed may vary. Rational and combinatorial approaches may be used to engineer soluble LIFR or gp130 polypeptides with novel properties, e.g., increased binding affinity and/or specificity for LIF. For example, to develop a soluble LIFR or gp130 polypeptide, a library of soluble LIFR or gp130 polypeptides may be created and screened, e.g., by bacterial display, phage display, yeast surface display, fluorescence-activated cell sorting (FACS), and/or any other suitable screening method.

Yeast surface display is a powerful combinatorial technology that has been used to engineer proteins with novel molecular recognition properties, increased target binding affinity, proper folding, and improved stability. In this platform, libraries of protein variants are generated and screened in a high-throughput manner to isolate mutants with desired biochemical and biophysical properties. As demonstrated in the Experimental section below, the present inventors have successfully employed yeast surface display for engineering soluble LIFR and gp130 polypeptides with increased binding affinities for LIF. Yeast surface display benefits from quality control mechanisms of the eukaryotic secretory pathway, chaperone-assisted folding, and efficient disulfide bond formation.

One example approach for developing a soluble LIFR or gp130 polypeptide having a desirable property of interest involves genetically fusing a soluble LIFR or gp130 polypeptide to the yeast mating agglutinin protein Aga2p, which is attached by two disulfide binds to the yeast cell wall protein Aga1p. This Aga2p-fusion construct, and a chromosomally integrated Aga1p expression cassette, may be expressed under the control of a suitable promoter, such as a galactose-inducible promoter. N- or C-terminal epitope tags may be included to measure cell surface expression levels by flow cytometry using fluorescently labeled primary or secondary antibodies. This construct represents the most widely used display format, where the N-terminus of the soluble LIFR or gp130 polypeptide may be fused to Aga2p, but several alternative variations of the yeast surface display plasmid have been described and may be employed to develop a soluble LIFR or gp130 polypeptide of the present disclosure. One of the benefits of this screening platform over panning-based methods used with phage or mRNA display is that two-color FACS can be used to quantitatively discriminate clones that differ by as little as two-fold in binding affinity to a particular target.

To selectively mutate LIFR or gp130 at the DNA level, an example approach is error prone PCR, which can be used to introduce mutations by any number of altered reaction conditions including using a polymerase that does not possess proofreading (i.e. exonuclease) activity, using mixtures of triphosphate derivatives of nucleoside analogues, using altered ratios of dNTPs, varying concentrations of magnesium or manganese, or the like. Alternatively, degenerate codons can be introduced by oligonucleotide assembly using, e.g., overlap extension PCR. Next, the genetic material may be amplified using flanking primers with sufficient overlap with the yeast display vector for homologous recombination in yeast. These methods allow LIFR or gp130 libraries to be created at relatively low cost and effort. Synthetic libraries and recent methods have been developed that allow defined control over library composition.

In certain aspects, a display library (e.g., a yeast display library) is screened for binding to the target of interest (e.g., LIF) by FACS. Two-color FACS may be used for library screening, where one fluorescent label can be used to detect a c-myc epitope tag and the other to measure interaction of the soluble LIFR or gp130 polypeptide against the binding target of interest. Different instrument lasers and/or filter sets can be used to measure excitation and emission properties of the two fluorophores at single-cell resolution. This enables yeast expression levels to be normalized with binding. That is, a soluble LIFR or gp130 polypeptide that exhibits poor yeast expression but binds a high amount of a target can be distinguished from a soluble LIFR or gp130 polypeptide that is expressed at high levels but binds weakly to a target. Accordingly, a two-dimensional flow cytometry plot of expression versus binding will result in a diagonal population of yeast cells that bind to target antigen. High-affinity binders can be isolated using library sort gates. Alternatively, in an initial sort round it could be useful to clear the library of undesired clones that do not express polypeptides of the desired length.

Following enrichment of soluble LIFR or gp130 polypeptide libraries for clones encoding soluble LIFR or gp130 polypeptides of interest, the yeast plasmids are recovered and sequenced. Additional rounds of FACS can be performed under increased sorting stringency. The binding affinities or kinetic off-rates of individual yeast-displayed LIFR or gp130 polypeptide clones may then be measured.

Once LIFR or gp130 polypeptides of interest have been identified by surface display (e.g., yeast surface display), the engineered soluble LIFR or gp130 polypeptides, or any fusion proteins including same, may be produced using a suitable method. In certain aspects, soluble LIFR or gp130 polypeptides or fusion proteins including same are produced using a recombinant DNA approach. Strategies have been developed for producing polypeptides using recombinant methods in a variety of host cell types. For example, functional soluble LIFR or gp130 polypeptides may be produced with barnase as a genetic fusion partner, which promotes folding in the *E. coli* periplasmic space and serves as a useful purification handle. According to certain embodiments, an engineered soluble LIFR or gp130 polypeptide is expressed in yeast (e.g., the yeast strain *Pichia pastoris* or *Saccharomyces cerevesiae*) or mammalian cells (e.g. human embryonic kidney cells or Chinese hamster ovary cells). The expression construct may encode one or more tags (e.g., a C-terminal hexahistadine tag for purification by, e.g., metal chelating chromatography (Ni-NTA)). Size exclusion chromatography may then be used to remove aggregates, misfolded multimers, and the like.

Aspects of the present disclosure include nucleic acids that encode the soluble LIFR and gp130 polypeptides (and any fusion proteins including same) of the present disclosure. That is, provided are nucleic acids that encode any of the soluble LIFR or gp130 polypeptides, or fusion proteins, of the present disclosure, including any of the soluble LIFR or gp130 polypeptides described herein. In certain aspects, such a nucleic acid is present in an expression vector. The expression vector includes a promoter operably linked to the nucleic acid encoding the agent (e.g., soluble LIFR or gp130 polypeptide), the promoter being selected based on the type of host cell selected to express the agent. Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance, neomycin resistance, and/or the like) to permit detection of those cells transformed with the desired DNA sequences.

Also provided are host cells that include a nucleic acid that encodes any of the soluble LIFR or gp130 polypeptides of the present disclosure, including any of the soluble LIFR or gp130 polypeptides described herein, as well as any expression vectors including the same. *Escherichia coli* is an example of a prokaryotic host cell that can be used for cloning a nucleic acid encoding a soluble LIFR or gp130 polypeptide of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the soluble LIFR and gp130 polypeptides of the present disclosure. Suitable mammalian host cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like.

Once synthesized (e.g., recombinantly), the soluble LIFR or gp130 polypeptide can be purified according to standard procedures known in the art, including ammonium sulfate precipitation, affinity columns, column chromatography, high performance liquid chromatography (HPLC) purification, gel electrophoresis, and the like. A subject soluble LIFR or gp130 polypeptide can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than the soluble LIFR or gp130 polypeptide, etc.

Compositions

Also provided are compositions that include a soluble LIFR and/or soluble gp130 polypeptide of the present disclosure, including any fusion and/or dimeric proteins including the same.

In certain aspects, the compositions include a soluble LIFR and/or soluble gp130 polypeptide of the present disclosure present in a liquid medium. The liquid medium may be an aqueous liquid medium, such as water, a buffered solution, and the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a protease inhibitor, glycerol, and the like may be present in such compositions.

Pharmaceutical compositions are also provided. The pharmaceutical compositions include any of the soluble LIFR polypeptides, soluble gp130 polypeptides, fusion proteins, and/or dimerized proteins of the present disclosure (any of which may be referred to herein as a "LIF-binding agent"), and a pharmaceutically-acceptable carrier. The pharmaceutical compositions generally include a therapeutically effective amount of the LIF-binding agent. By "therapeutically effective amount" is meant a dosage sufficient to produce a desired result, e.g., an amount sufficient to effect beneficial or desired therapeutic (including preventative) results, such as a reduction in cellular proliferation in an individual having a cell proliferative disorder (e.g., cancer, such as pancreatic cancer) associated with LIF signaling.

A LIF-binding agent of the present disclosure can be incorporated into a variety of formulations for therapeutic administration. More particularly, the LIF-binding agent can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the LIF-binding agents of the present disclosure suitable for administration to an individual (e.g., suitable for human administration) are generally sterile and may further be free of detectable pyrogens or other contaminants contraindicated for administration to an individual according to a selected route of administration.

In pharmaceutical dosage forms, the LIF-binding agent can be administered alone or in appropriate association, as well as in combination, with other pharmaceutically-active compounds. The following methods and excipients are merely examples and are in no way limiting.

For oral preparations, the LIF-binding agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The LIF-binding agents can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the LIF-binding agent may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods of Use

Also provided are methods of using the soluble LIFR polypeptides, soluble gp130 polypeptides, fusion proteins, and/or dimerized proteins of the present disclosure (any of which may be referred to herein as a "LIF-binding agent"). According to certain embodiments, provided are methods that include administering to an individual in need thereof a therapeutically effective amount of a soluble LIFR polypeptide, soluble gp130 polypeptide, fusion protein, and/or dimerized protein of the present disclosure, or pharmaceutical composition including any such LIF-binding agents. In certain aspects, the individual in need thereof has a cell proliferative disorder associated with LIF signaling, and the administering is effective in treating the cell proliferative disorder. In certain aspects, the cell proliferative disorder is cancer. Cancers of interest include, but are not limited to, pancreatic cancers.

For example, in some embodiments, a LIF-binding agent or pharmaceutical composition of the present disclosure inhibits growth, metastasis and/or invasiveness of a cancer cell(s) in a host when the LIF-binding agent or pharmaceutical composition is administered in an effective amount. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like.

Cancers which may be treated using the methods of the present disclosure include, but are not limited to, solid tumors, lung cancer (e.g., non-small cell lung cancer (NSCLC), breast cancer, prostate cancer, pancreatic cancer, colorectal carcinoma, renal cell carcinoma, and any other type of cancer which may be treated using a LIF-binding agent or pharmaceutical composition of the present disclosure.

The LIF-binding agent may be administered alone (e.g., in monotherapy) or in combination (e.g., in combination therapy) with one or more additional therapeutic agents.

In some embodiments, an effective amount of the LIF-binding agent (or pharmaceutical composition including same) is an amount that, when administered alone (e.g., in monotherapy) or in combination (e.g., in combination therapy) with one or more additional therapeutic agents, in one or more doses, is effective to reduce the symptoms of a cell proliferative disorder (e.g., cancer) in the individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the LIF-binding agent or pharmaceutical composition.

In certain aspects, the methods of the present disclosure inhibit growth, metastasis and/or invasiveness of cancer cells in the individual when the LIF-binding agent or pharmaceutical composition is administered in an effective amount.

The LIF-binding agent or pharmaceutical composition may be administered to an individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the LIF-binding agent and/or the desired effect. The LIF-binding agents or pharmaceutical compositions may be administered in a single dose or in multiple doses. In some embodiments, the LIF-binding agent or pharmaceutical composition is administered intravenously. In some embodiments, the LIF-binding agent or pharmaceutical composition is administered by injection, e.g., for systemic delivery (e.g., intravenous infusion) or to a local site.

A variety of individuals are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual will be human.

By "treating" or "treatment" is meant at least an amelioration of the symptoms associated with the cell proliferative disorder (e.g., cancer) of the individual, where amelioration is used in a broad sense to refer to at least a reduction in the magnitude of a parameter, e.g. symptom, associated with the cell proliferative disorder being treated. As such, treatment also includes situations where the cell proliferative disorder, or at least symptoms associated therewith, are completely inhibited, e.g., prevented from happening, or stopped, e.g., terminated, such that the individual no longer suffers from the cell proliferative disorder, or at least the symptoms that characterize the cell proliferative disorder.

Dosing is dependent on severity and responsiveness of the disease state to be treated. Optimal dosing schedules can be calculated from measurements of drug accumulation in the body of the patient. The administering physician can determine optimum dosages, dosing methodologies and repetition rates. Optimum dosages may vary depending on the relative potency of individual LIF-binding agents, and can generally be estimated based on $EC_{50}$s found to be effective in in vitro and in vivo animal models, etc. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the LIF-binding agent or pharmaceutical composition is administered in maintenance doses, ranging from 0.01 μg to 100 g per kg of body weight, once or more daily, to once every several months, once every six months, once every year, or at any other suitable frequency.

The therapeutic methods of the present disclosure may include administering a single type of LIF-binding agent to a subject, or may include administering two or more types of LIF-binding agents to a subject by administration of a cocktail of different LIF-binding agents.

In some embodiments, provided are methods that include identifying an individual as having a cell proliferative disorder associated with LIF signaling. Identifying the individual as having a cell proliferative disorder associated with LIF signaling may be carried out using a variety of approaches and combinations thereof. In certain aspects, the identifying is based on LIF abundance in a sample (e.g., a fluid sample, tumor biopsy, and/or the like) obtained from the individual. In some embodiments, the LIF abundance is quantified using a soluble LIFR polypeptide, soluble gp130 polypeptide, fusion protein, and/or dimerized protein of the present disclosure, as a LIF capture agent.

In certain aspects, the identifying is based on the level of LIF signaling in a sample obtained from the individual. The level of LIF signaling may be based on the phosphorylation status of one or more LIF signaling pathway molecules, including a molecule in the Jak-STAT signaling pathway, a non-limiting example of which is pSTAT3 (e.g., pSTAT3-Y705). According to certain embodiments, the identifying is based on an immunoassay. A variety of suitable immunoassay formats are available, including ELISA, flow cytometry assays, immunohistochemistry on tissue section samples, immunofluorescence on tissue section samples, Western analysis, and/or the like.

In some embodiments, the identifying is based on nucleic acid sequencing. For example, the number of sequencing reads corresponding to an mRNA encoding a protein of interest may be used to determine the expression level of the protein. In certain aspects, the sequencing is performed using a next-generation sequencing system, such as on a sequencing platform provided by Illumina® (e.g., the HiSeq™, MiSeq™ and/or Genome Analyzer™ sequencing systems); Oxford Nanopore Technologies (e.g., a MinION™ GridIONx5™, PromethION™, or SmidgION™ nanopore sequencing device), Ion Torrent™ (e.g., the Ion PGM™ and/or Ion Proton™ sequencing systems); Pacific Biosciences (e.g., the PACBIO RS II sequencing system); Life Technologies™ (e.g., a SOLID sequencing system); Roche (e.g., the 454 GS FLX+ and/or GS Junior sequencing systems); or any other sequencing platform of interest. Protocols for isolating nucleic acids from tissue or fluid samples, as well as protocols for preparing sequencing libraries having sequencing adapters appropriate for the desired sequencing platform are readily available.

In some embodiments, methods that include identifying the individual as having a cell proliferative disorder associated with LIF signaling further include obtaining the sample from the individual.

The sample obtained from the individual may be any sample suitable for determining whether the individual has a cell proliferative disorder associated with LIF signaling. In certain aspects, the sample is a fluid sample, such as whole blood, serum, plasma, or the like. In some embodiments, the sample is a tissue sample. Tissue samples of interest include, but are not limited to, tumor biopsy samples, and the like.

Kits

Also provided by the present disclosure are kits. In some embodiments, provided are kits that include a pharmaceutical composition that includes any of the soluble LIFR polypeptides, soluble gp130 polypeptides, fusion proteins, and/or dimerized proteins of the present disclosure. The kits may further include instructions for administering the pharmaceutical composition to an individual in need thereof, e.g., an individual having a cell-proliferative disorder (e.g., cancer, such as pancreatic cancer) or other medical condition for which inhibition of LIF activity would be beneficial. In certain aspects, a kit includes the pharmaceutical composition present in one or more (e.g., two or more) unit dosages.

In certain aspects, provided are kits that include any of the soluble LIFR polypeptides, soluble gp130 polypeptides, fusion proteins, and/or dimerized proteins of the present disclosure, where such kits further include instructions for using same to detect LIF in a sample (e.g., a fluid sample, tissue sample, and/or the like).

In some embodiments, provided are kits that include any of the soluble LIFR polypeptides, soluble gp130 polypeptides, fusion proteins, and/or dimerized proteins of the present disclosure, where such kits further include instructions for using same to inhibit LIF signaling/activity in vitro or in vivo, e.g., for research purposes.

Components of the kits may be present in separate containers, or multiple components may be present in a single container. A suitable container includes a single tube (e.g., vial), one or more wells of a plate (e.g., a 96-well plate, a 384-well plate, etc.), or the like.

The instructions of the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Notwithstanding the appended claims, the present disclosure is also defined by the following clauses:

1. A soluble leukemia inhibitory factor receptor (LIFR) polypeptide comprising an amino acid sequence that is at least 70% identical to SEQ ID NO:2, wherein the LIFR polypeptide exhibits increased binding affinity for leukemia inhibitory factor (LIF) relative to a corresponding wild-type LIFR polypeptide.
2. The soluble LIFR polypeptide of clause 1, comprising one or both of:
   an amino acid substitution at position L218, and
   an amino acid substitution at position N277,
   wherein identification of positions is relative to SEQ ID NO:2.
3. The soluble LIFR polypeptide of clause 2, comprising one or both of:
   a L218P amino acid substitution, and
   a N277D amino acid substitution.
4. The soluble LIFR polypeptide of any one of clauses 1 to 3, comprising one, two, or each of:
   an amino acid substitution at position 1257,
   an amino acid substitution at position V262, and
   an amino acid substitution at position T273,
   wherein identification of positions is relative to SEQ ID NO:2.
5. The soluble LIFR polypeptide of clause 4, comprising one, two, or each of:
   a I257V amino acid substitution,
   a V262A amino acid substitution, and
   a T273I amino acid substitution.
6. The soluble LIFR polypeptide of any one of clauses 1 to 5, comprising one, two, or each of:
   an amino acid substitution at position 1217,
   an amino acid substitution at position H240, and
   an amino acid substitution at position 1260,
   wherein identification of positions is relative to SEQ ID NO:2.
7. The soluble LIFR polypeptide of clause 6, comprising one, two, or each of:
   a I217V amino acid substitution,
   a H240R amino acid substitution, and
   a I260V amino acid substitution.
8. The soluble LIFR polypeptide of any one of clauses 1 to 7, comprising an amino acid substitution at position N242, wherein identification of the position is relative to SEQ ID NO:2.
9. The soluble LIFR polypeptide of clause 8, comprising a N242D amino acid substitution.
10. The soluble LIFR polypeptide of any one of clauses 1 to 9, comprising an amino acid sequence that is at least 80% identical to SEQ ID NO:2.
11. The soluble LIFR polypeptide of any one of clauses 1 to 9, comprising an amino acid sequence that is at least 90% identical or at least 95% identical to SEQ ID NO:2.
12. The soluble LIFR polypeptide of any one of clauses 1 to 11, wherein the soluble LIFR polypeptide is fused to one or more heterologous polypeptides.
13. The soluble LIFR polypeptide of clause 12, wherein the one or more heterologous polypeptides comprises a heterologous polypeptide selected from the group consisting of: an Fc domain, an albumin, a transferrin, XTEN, a homo-amino acid polymer, a proline-alanine-serine polymer, an elastin-like peptide, and any combination thereof.
14. The soluble LIFR polypeptide of clause 13, wherein the one or more heterologous polypeptides comprises an Fc domain.
15. The soluble LIFR polypeptide of any one of clauses 12 to 14, wherein the one or more heterologous polypeptides comprises the soluble gp130 polypeptide of any one of clauses 27 to 38.
16. The soluble LIFR polypeptide of clause 15, wherein the soluble LIFR polypeptide and soluble gp130 polypeptide are fused via a linker.
17. The soluble LIFR polypeptide of clause 16, wherein the linker comprises a GlySer linker.
18. The soluble LIFR polypeptide of clause 17, wherein the GlySer linker comprises a $(Gly4Ser)_n$ linker.
19. The soluble LIFR polypeptide of any one of clauses 1 to 18, dimerized with a soluble LIFR polypeptide of any one of clauses 1 to 18.
20. The soluble LIFR polypeptide of clause 19, wherein each soluble LIFR polypeptide comprises an Fc domain, and dimerization is via the Fc domain.
21. A nucleic acid encoding the soluble LIFR polypeptide of any one of clauses 1 to 18.
22. An expression vector comprising the nucleic acid of clause 21.
23. A cell comprising:
   the soluble LIFR polypeptide of any one of clauses 1 to 18,
   the nucleic acid of clause 21,
   the expression vector of clause 22, or
   any combination thereof.
24. A method of producing the soluble LIFR polypeptide of any one of clauses 1 to 18, comprising:
   culturing a cell comprising the expression vector of clause 22 under conditions in which the cell produces the LIFR polypeptide.
25. The method according to clause 24, further comprising, prior to culturing the cell, introducing the expression vector into the cell.
26. The method according to clause 24 or clause 25, further comprising, subsequent to culturing the cell, purifying the LIFR polypeptide from the cell.
27. A soluble glycoprotein 130 (gp130) polypeptide comprising an amino acid sequence that is at least 70% identical to SEQ ID NO:4, wherein the gp130 polypeptide exhibits increased binding affinity for leukemia inhibitory factor (LIF) relative to a corresponding wild-type gp130 polypeptide.

28. The soluble gp130 polypeptide of clause 27, comprising an amino acid substitution at position K45, wherein identification of the position is relative to SEQ ID NO:4.
29. The soluble gp130 polypeptide of clause 28, comprising a K45E amino acid substitution.
30. The soluble gp130 polypeptide of any one of clauses 27 to 29, comprising one or both of:
    an amino acid substitution at position Y95, and
    an amino acid substitution at position K184,
    wherein identification of positions is relative to SEQ ID NO:4.
31. The soluble gp130 polypeptide of clause 30, comprising one or both of:
    a Y95D amino acid substitution, and
    a K184E amino acid substitution.
32. The soluble gp130 polypeptide of any one of clauses 27 to 31, comprising one or both of:
    an amino acid substitution at position F46, and
    an amino acid substitution at position 1130,
    wherein identification of positions is relative to SEQ ID NO:4.
33. The soluble gp130 polypeptide of clause 32, comprising one or both of:
    a F46L amino acid substitution, and
    a I130M amino acid substitution.
34. The soluble gp130 polypeptide of any one of clauses 27 to 33, comprising an amino acid sequence that is at least 80% identical to SEQ ID NO:4.
35. The soluble gp130 polypeptide of any one of clauses 27 to 33, comprising an amino acid sequence that is at least 90% identical, or at least 95% identical to SEQ ID NO:4.
36. The soluble gp130 polypeptide of any one of clauses 27 to 35, wherein the soluble gp130 polypeptide is fused to one or more heterologous polypeptides.
37. The soluble gp130 polypeptide of clause 36, wherein the one or more heterologous polypeptides comprises a heterologous polypeptide selected from the group consisting of: an Fc domain, an albumin, a transferrin, XTEN, a homo-amino acid polymer, a proline-alanine-serine polymer, an elastin-like peptide, and any combination thereof.
38. The soluble gp130 polypeptide of clause 37, wherein the one or more heterologous polypeptides comprises an Fc domain.
39. The soluble gp130 polypeptide of any one of clauses 36 to 38, wherein the one or more heterologous polypeptides comprises the soluble LIFR polypeptide of any one of Clauses 1 to 14.
40. The soluble gp130 polypeptide of clause 39, wherein the soluble gp130 polypeptide and soluble LIFR polypeptide are fused via a linker.
41. The soluble gp130 polypeptide of clause 40, wherein the linker comprises a GlySer linker.
42. The soluble gp130 polypeptide of clause 41, wherein the GlySer linker comprises a $(Gly4Ser)_n$ linker.
43. The soluble gp130 polypeptide of any one of clauses 27 to 42, dimerized with a soluble gp130 polypeptide of any one of clauses 27 to 42.
44. The soluble gp130 polypeptide of clause 43, wherein each soluble gp130 polypeptide comprises an Fc domain, and dimerization is via the Fc domain.
45. A nucleic acid encoding the soluble gp130 polypeptide of any one of clauses 27 to 42.
46. An expression vector comprising the nucleic acid of clause 45.
47. A cell comprising:
    the soluble gp130 polypeptide of any one of clauses 27 to 42,
    the nucleic acid of clause 45,
    the expression vector of clause 46, or
    any combination thereof.
48. A method of producing the soluble gp130 polypeptide of any one of clauses 27 to 42, comprising:
    culturing a cell comprising the expression vector of clause 46 under conditions in which the cell produces the soluble gp130 polypeptide.
49. The method according to clause 48, further comprising, prior to culturing the cell, introducing the expression vector into the cell.
50. The method according to clause 48 or clause 49, further comprising, subsequent to culturing the cell, purifying the soluble gp130 polypeptide from the cell.
51. A heterodimeric protein, comprising:
    the soluble LIFR polypeptide of any one of clauses 1 to 14, dimerized with the soluble gp130 polypeptide of any one of clauses 27 to 38.
52. The heterodimeric protein of clause 51, wherein the soluble LIFR polypeptide and the soluble gp130 polypeptide each comprise a dimerization domain through which the soluble LIFR polypeptide and the soluble gp130 polypeptide are dimerized.
53. The heterodimeric protein of clause 52, wherein the dimerization domain comprises an Fc domain.
54. A pharmaceutical composition, comprising:
    a soluble leukemia inhibitory factor receptor (LIFR) polypeptide which binds to leukemia inhibitory factor (LIF) and comprises an amino acid sequence that is at least 70% identical to SEQ ID NO:2; and
    a pharmaceutically-acceptable carrier.
55. A pharmaceutical composition, comprising:
    a soluble glycoprotein 130 (gp130) polypeptide which binds to leukemia inhibitory factor (LIF) and comprises an amino acid sequence that is at least 70% identical to SEQ ID NO:4; and
    a pharmaceutically-acceptable carrier.
56. A pharmaceutical composition, comprising:
    a soluble leukemia inhibitory factor receptor (LIFR) polypeptide which binds to leukemia inhibitory factor (LIF) and comprises an amino acid sequence that is at least 70% identical to SEQ ID NO:2, dimerized with
    a soluble glycoprotein 130 (gp130) polypeptide which binds to leukemia inhibitory factor (LIF) and comprises an amino acid sequence that is at least 70% identical to SEQ ID NO:4; and
    a pharmaceutically-acceptable carrier.
57. A pharmaceutical composition, comprising:
    the soluble LIFR polypeptide of any one of clauses 1 to 18; and
    a pharmaceutically-acceptable carrier.
58. A pharmaceutical composition, comprising:
    the soluble gp130 polypeptide of any one of clauses 27 to 42; and
    a pharmaceutically-acceptable carrier.
59. A pharmaceutical composition, comprising:
    the heterodimeric protein of any one of clauses 51 to 53; and
    a pharmaceutically-acceptable carrier.
60. A method comprising administering a therapeutically effective amount of the pharmaceutical composition of any one of clauses 54 to 59 to an individual in need thereof.

61. The method according to clause 60, wherein the individual in need thereof is an individual having cancer.
62. The method according to clause 61, wherein the cancer is pancreatic cancer.
63. A kit comprising:
    the pharmaceutical composition of any one of clauses 54 to 59; and
    instructions for administering the pharmaceutical composition to an individual in need thereof.
64. The kit of clause 63, wherein the pharmaceutical composition is present in one or more unit dosages.
65. The kit of clause 63, wherein the pharmaceutical composition is present in two or more unit dosages.
66. The kit of any one of clauses 63 to 65, wherein the individual in need thereof is an individual having cancer.
67. The kit of clause 66, wherein the cancer is pancreatic cancer.

The following examples are offered by way of illustration and not by way of limitation.

EXPERIMENTAL

Example 1—Engineered Soluble LIFR Polypeptides

In this example, LIFR variants were identified from libraries of the Ig-like domain of human LIFR displayed on the surface of yeast and sorted using FACS for optimal binders to human LIF. After multiple rounds of sorting, variants were selected, sequenced, and characterized. LIFR variants isolated from the sorts are summarized in FIG. 3.

Figure 3:
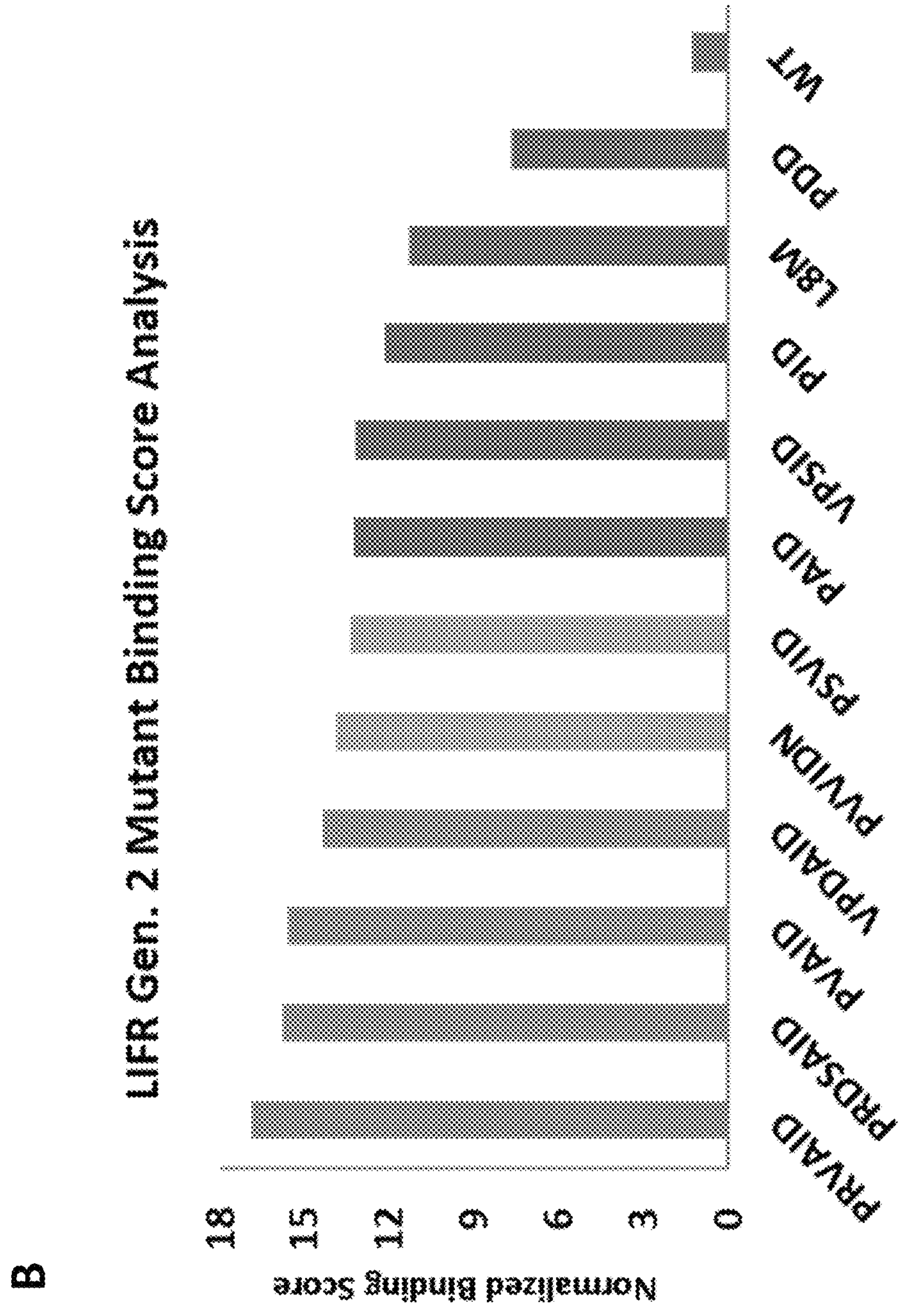
FIG. 3 Panel A: Consensus mutations observed in LIFR Ig-like domain variants isolated across multiple sorts. Panel B: Binding scores of LIFR variants calculated from normalized, summed fluorescence binding values at low (10 pM, 100 pM) LIF concentrations. All scores were normalized to wild-type and for differential expression on the surface of yeast.

FIG. 3, panel A, shows consensus mutations observed in LIFR Ig-like domain variants isolated across multiple sorts. Numbering starts at the beginning of the LIFR Cytokine Binding Motif I (CBMI) domain. FIG. 3, panel B, shows binding scores of LIFR variants calculated from normalized, summed fluorescence binding values at low (10 pM, 100 pM) LIF concentrations. All scores were normalized to wild-type and for differential expression on the surface of yeast.

Figure 4:
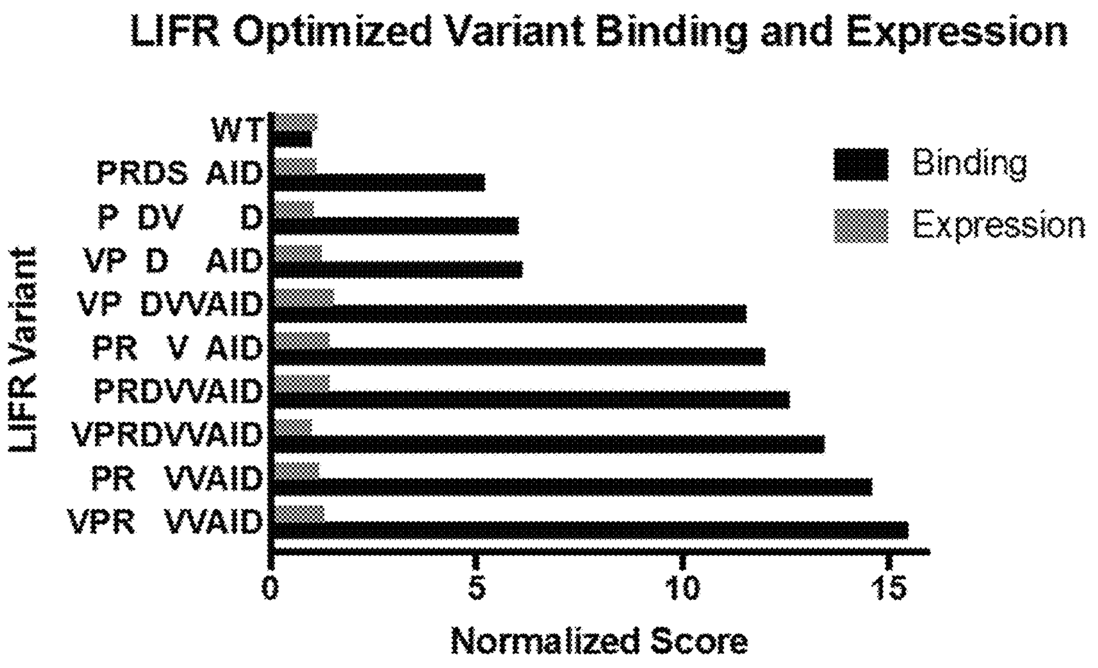
FIG. 4 Panel A: Summary of LIFR variants generated using site-directed mutagenesis. Panel B: Binding score of LIFR variants. Expression normalized to wild-type (WT) is also shown.

Based on the identified LIFR mutations (shown in FIG. 3, panel A), multiple combinations of possible mutant LIFR variants which were not observed in any sorts were created using site-directed mutagenesis. FIG. 4, panel A, summarizes the variants generated using site-directed mutagenesis. FIG. 4, panel B, shows the binding scores of such variants calculated as described above for FIG. 3, panel B. Expression normalized to wild-type (WT) is also shown. From this analysis, VPRVVAID (I217V-L218P-H240R-I257V-I206V-V262A-T273I-N277D) was identified as the optimal LIFR variant.

Figure 5:
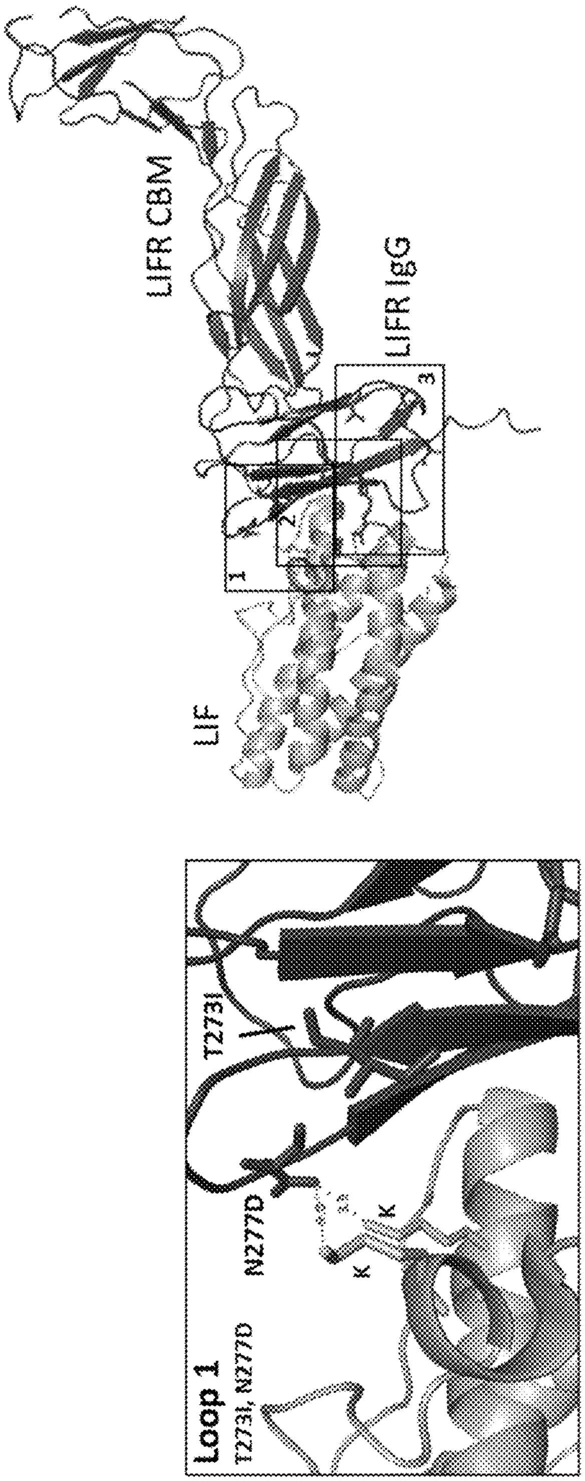
FIG. 5 Consensus mutations from FIG. 4, panel A, shown in a PyMOL modeled structure of human LIF (pink) binding to human LIFR (blue). Mutations are shown in red, and are introduced using PyMOL. Clusters of mutations in loops 1, 2, and 3 are enlarged in insets.
Figure 5:
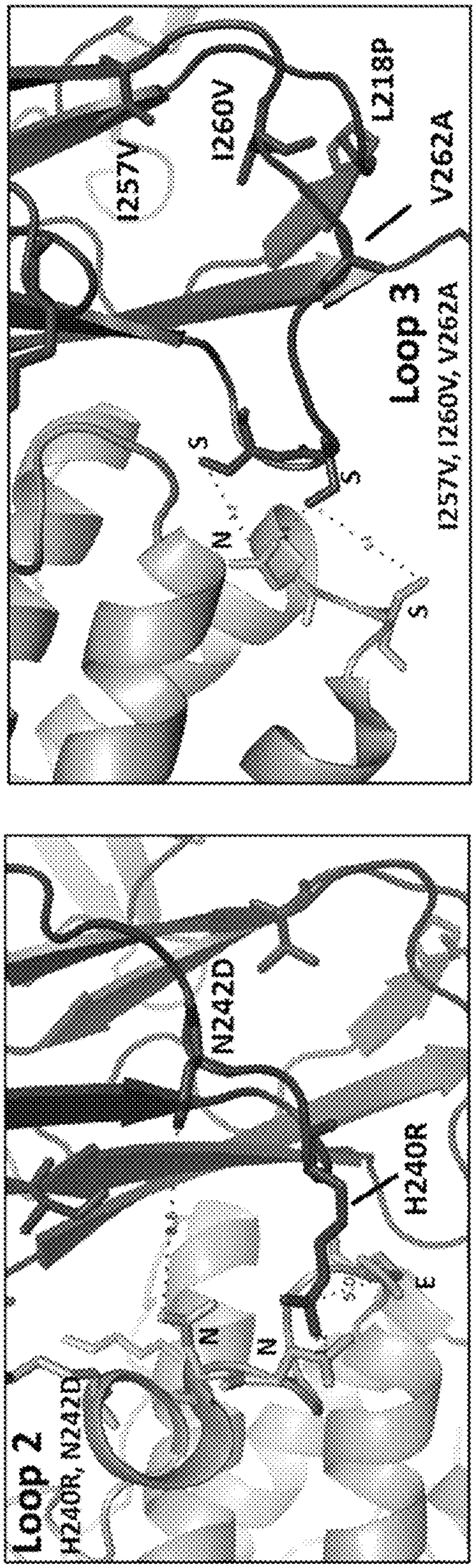

In FIG. 5, consensus mutations from FIG. 4, panel A, are shown in a PyMOL modeled structure of human LIF (pink) binding to human LIFR (blue). Mutations are shown in red, and are introduced using PyMOL. Clusters of mutations in loops 1, 2, and 3 are enlarged in insets.

Example 2—Engineered Soluble gp130 Polypeptides

In this example, gp130 variants were identified from libraries of the CBM domain of human gp130 displayed on the surface of yeast and sorted using FACS for optimal binders to human LIF. After multiple rounds of sorting, variants were selected, sequenced, and characterized. gp130 variants isolated from the sorts are summarized in FIG. 6.

Figure 6:
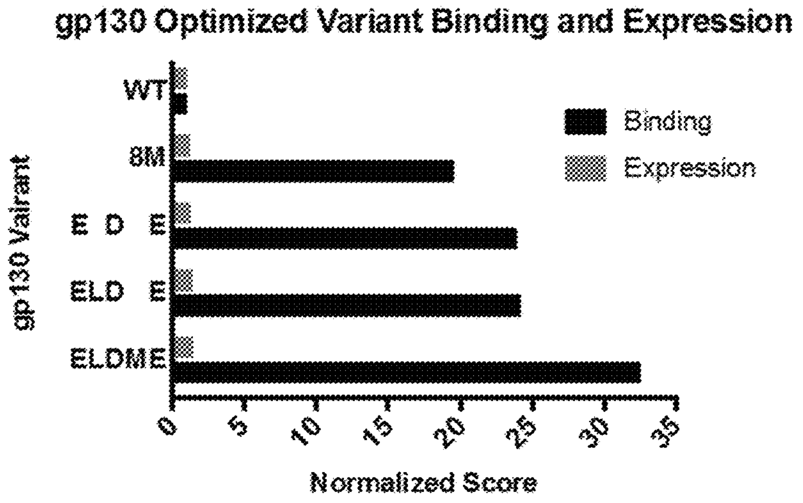
FIG. 6 Panel A: Consensus mutations observed in gp130 CBM domain variants isolated across multiple sorts. Panel B: Summary of mutant gp130 variants created using site-directed mutagenesis. Panel C: Binding scores of gp130 variants. Expression normalized to wild-type (WT) is also shown.

FIG. 6, panel A, shows consensus mutations observed in gp130 CBM domain variants isolated across multiple sorts. Numbering starts at the beginning of the gp130 Cytokine Binding Motif (CBM) domain. FIG. 6, panel B, shows a summary of mutant gp130 variants created using site-directed mutagenesis. FIG. 6, panel C, shows the binding scores of gp130 variants calculated as described in FIG. 3, panel B, using 100 pM and 1 nM as low LIF concentrations. Expression normalized to wild-type (WT) is also shown. From this analysis, ELDME (K45E-F46L-Y95D-I130M-K184E) was identified as the optimal gp130 variant.

Figure 7:
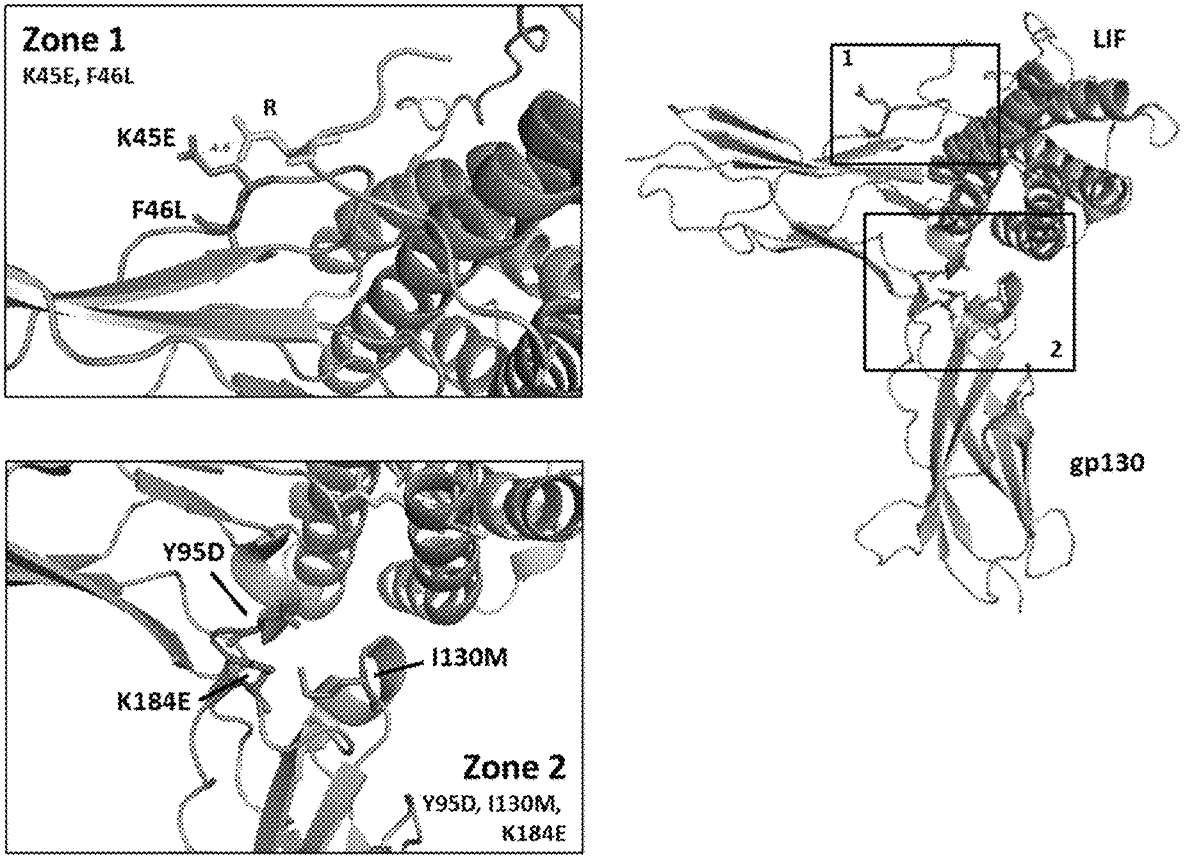
FIG. 7 Consensus mutations in the gp130 ELDME structure. Selection of consensus mutations from FIG. 6, panel A, shown in the solved structure of human LIF (blue) binding to human gp130 (pink). Mutations, inserted using PyMOL, are shown in teal. Clusters of mutations in zones 1 and 2 are enlarged in insets.

In FIG. 7, selected consensus mutations from FIG. 6, panel A, are shown in the solved structure of human LIF (blue) binding to human gp130 (pink). Mutations, inserted using PyMOL, are shown in teal. Clusters of mutations in zones 1 and 2 are enlarged in insets.

Example 3—Binding of LIFR and gp130 Variants to Human LIF

In this example, LIFR or gp130 variants were displayed on the surface of yeast. Binding to human LIF was measured via fluorescent antibody detection using flow cytometry.

Figure 8:
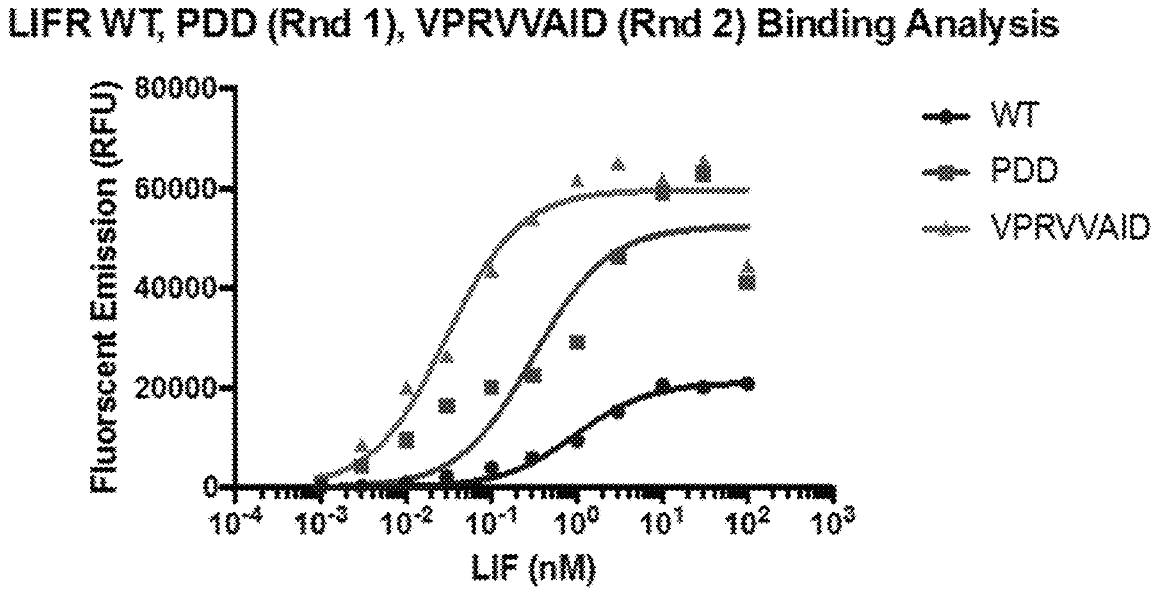
FIG. 8 Binding of yeast displayed LIFR VPRVVAID and gp130 ELDME to human LIF. Panel A: LIFR wild-type (WT) (circles), the "PDD" variant (L218P-N42D-N277D) (squares), and the VPRVVAID variant (mutations in FIG. 4, panel A) (triangles) binding to human LIF. The $K_D$ of the VPRVVAID variant was measured at 30 pM, which is 32-fold higher affinity compared to wild-type (WT). Panel B: gp130 wild-type (WT) (circles), the "8M" variant (E4K-K5R-N14D-K45E-F46L-K83R-Y95D-N100S) (squares), and the ELDME variant (mutations in FIG. 4, panel A) (triangles) binding to human LIF. The $K_D$ of the ELDME variant was measured at 5 nM, which is 12-fold higher affinity compared to wild-type (WT).
Figure 8:
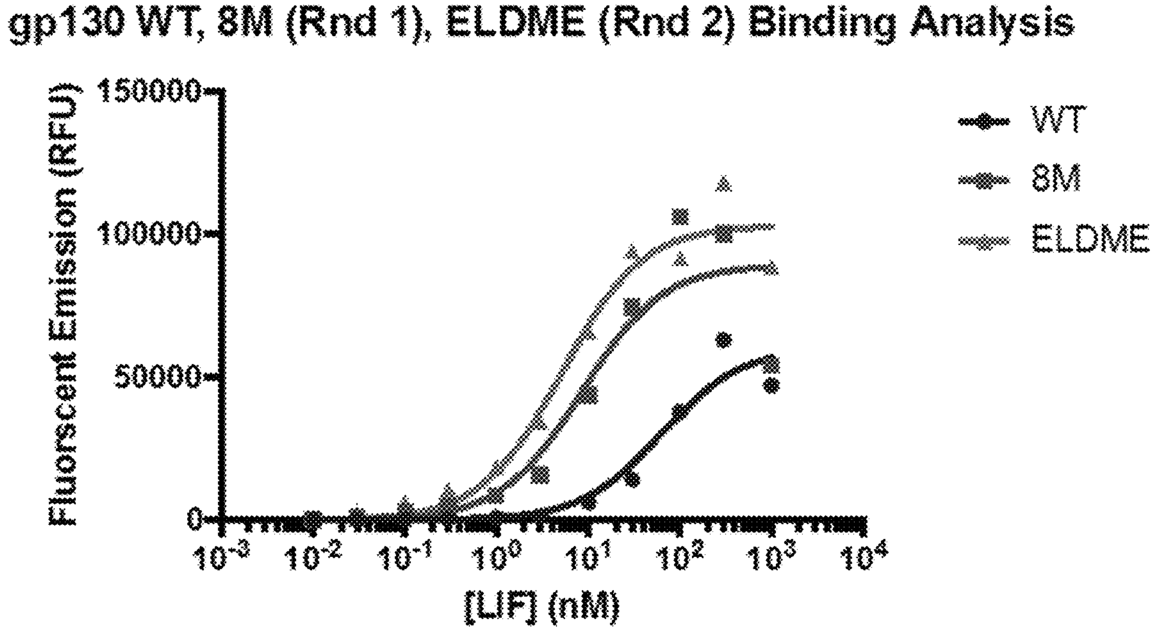

FIG. 8, panel A, shows binding results of yeast displayed wild-type LIFR and LIFR variants to human LIF. Results for LIFR wild-type (WT) (circles), the "PDD" variant (L218P-N42D-N277D) (squares), and the VPRVVAID variant (mutations in FIG. 4, panel A) (triangles) are shown. The $K_D$ of the VPRVVAID variant was measured at 30 pM, which is 32-fold higher affinity compared to wild-type (WT).

FIG. 8, panel B, shows binding results of yeast displayed wild-type gp130 and gp130 variants to human LIF. Results for gp130 wild-type (WT) (circles), the "8M" variant (E4K-K5R-N14D-K45E-F46L-K83R-Y95D-N100S) (squares), and the ELDME variant (mutations in FIG. 4, panel A) (triangles) are shown. The $K_D$ of the ELDME variant was measured at 5 nM, which is 12-fold higher affinity compared to wild-type (WT).

Figure 9:
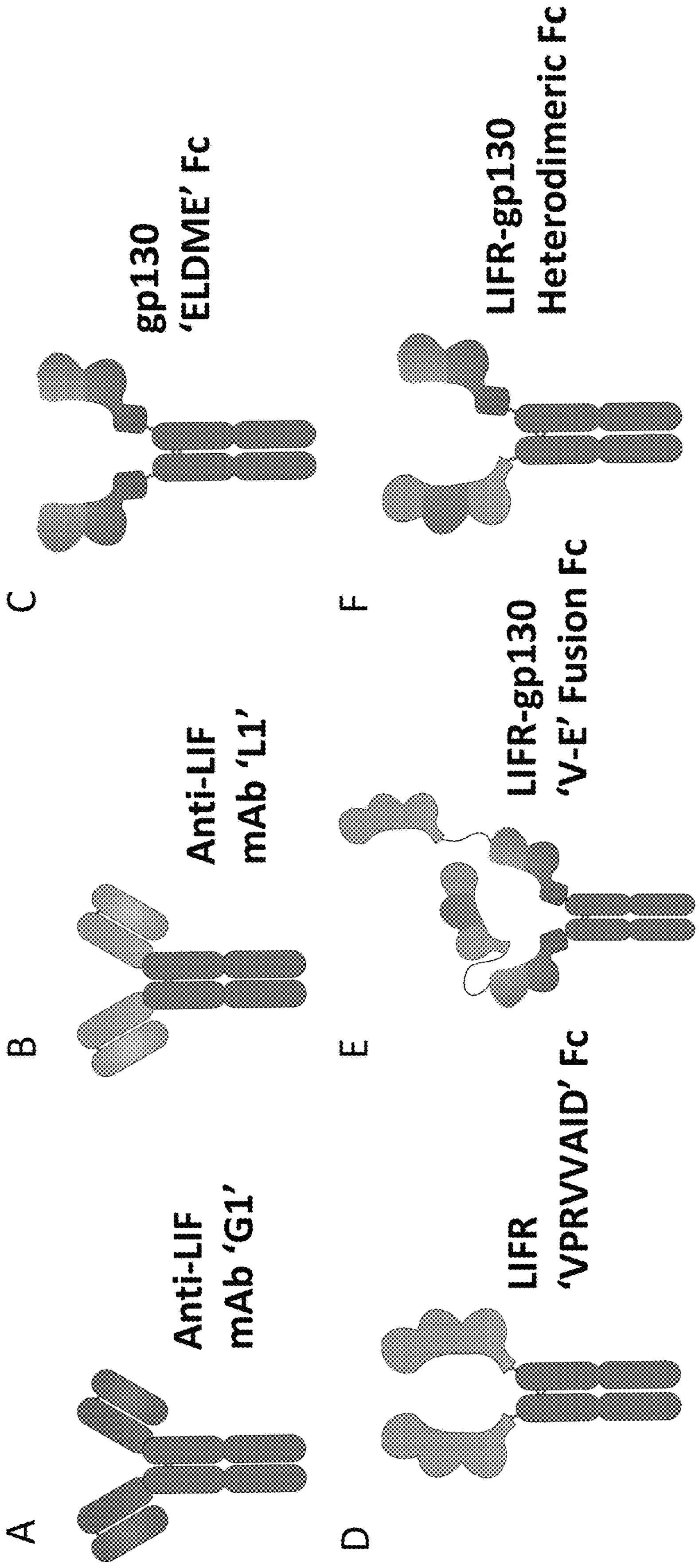
FIG. 9 Schematic illustration of example homodimeric and heterodimeric soluble LIFR and/or gp130 fusion constructs of the present disclosure (Panels C-F). Panel A: Anti-LIF monoclonal antibody 'G1' which targets the gp130-binding face. Panel B: Anti-LIF monoclonal antibody 'L1' which targets the LIFR-binding face. Panel C: gp130 CBM domain (ELDME) Fc-fusion. Panel D: LIFR CBMI-Ig-like-CBMII domains (VPRVVAID) Fc-fusion. Panel E: LIFR CBMI-Ig-like-CBMII domains (VPRVVAID)— gp130 CBM domain (ELDME) Fc-fusion. This is a homodimer, with LIFR and gp130 fused using a 5× Gly4Ser linker. Panel F: LIFR CBMI-Ig-like-CBMII domains (VPRVVAID)—gp130 CBM domain (ELDME) Heterodimeric Fc-fusion. This variant has LIFR on one arm and gp130 on the other arm of the Fc. All variants were successfully expressed and purified.

Example 4—Homodimeric and Heterodimeric Soluble LIFR and gp130 Fusion Polypeptides In this example, homodimeric and heterodimeric soluble LIFR and/or gp130 Fc fusion constructs were generated. FIGS. 9, panels A and B, schematically illustrate the Anti-LIF monoclonal antibodies G1 and L1, which target the gp130- and LIFR-binding faces of LIF, respectively. These antibodies serve as benchmarks for efficacy.

Schematically illustrated in FIG. 9, panel C, is a gp130 cytokine binding motif (CBM) variant (ELDME) Fc-fusion homodimer, where dimerization is via the Fc domain. This construct may be referred to as "gp130 ELDME Fc".

FIG. 9, panel D, schematically illustrates a LIFR cytokine binding motif 1—Ig-like—cytokine binding motif 2 (CBMI-Ig-like-CBMII) variant (VPRVVAID) Fc-fusion homodimer, where dimerization is via the Fc domain. This construct may be referred to as "LIFR VPRVVAID Fc".

Schematically illustrated in FIG. 9, panel E, is a homodimer where each monomer includes the LIFR CBMI-Ig-like-CBMII VPRVVAID variant fused to the gp130 CBM ELDME variant via a 5× Gly4Ser linker. An Fc domain is C-terminal to the gp130 portion and dimerization is via the Fc domain. This construct may be referred to as "LIFR-gp130 V-E fusion Fc".

FIG. 9, panel F, schematically illustrates a heterodimer that includes a gp130 ELDME Fc monomer as shown in panel C and a LIFR VPRVVAID Fc monomer as shown in panel D, dimerized via the Fc domain.

Each of the constructs schematically illustrated in FIG. 9, panels C-F, were successfully expressed and purified.

Binding of the purified LIF inhibitors to soluble LIF was tested using KinExA. Shown in FIG. 10 are binding results for: (1) a homodimer having a WT LIFR CBMI-Ig-like-CBMII Fc fusion as each monomer; (2) a homodimer having LIFR VPRVVAID Fc as each monomer; and (3) a homodimer having LIFR-gp130 V-E fusion Fc as each monomer. $K_D$ values calculated from KinExA software and fitted curves are shown. LIFR-VPRVVAID-Fc has an affinity of 23 pM for human LIF, a 43 fold improvement over LIFR-WT-Fc.

Example 5—Multiple LIF Binding Assay

A binding assay was performed as schematically illustrated in FIG. 11, panel A to determine if the receptor decoys bound to LIF can also engage another LIF molecule. The goal was to demonstrate whether inhibitors that are homodimers as Fc-fusions are able to bind to LIF with each arm of the dimer, simultaneously. According to the assay, LIF is displayed on the surface of yeast. Fc-fusion inhibitors (LIFR-VPRVVAID-Fc depicted) are introduced at saturating concentrations, allowed to bind to the displayed ligand, and excess is washed away. Soluble LIF-His is then co-incubated with Fc-fusion-bound yeast. LIF binding is detected via the His-tag domain of LIF-His, which should only be present if multiple LIF binding to the Fc-fusion occurs, with the homodimer acting as a 'bridge.'

Results of the multiple LIF binding assay are shown in FIG. 11, panel B. LIF was displayed on yeast with Fc-fusion inhibitors used as a binding bridge between displayed and soluble LIF. Fluorescent emission from an anti-His6 tag fluorescent antibody in each condition was normalized to no LIF-His added controls. Fc-fusion binding to displayed LIF was also confirmed using an anti-Fc tag fluorescent antibody (data shown in FIG. 12, panel B). Multiple LIF binding results for LIFR-WT-Fc, LIFR-VPRVVAID-Fc, LIFR-gp130 Fusion-Fc, and Anti-LIF mAb L1 are shown.

From these results, it is determined that all four homodimers tested can bind to multiple LIF molecules. Engineered LIFR-Fc shows improved multi-LIF binding over LIFR-WT-Fc, likely due to improved affinity for LIF and a slower off-rate (discussed in Example 6). The LIFR-gp130 Fusion-Fc shows the greatest multi-LIF binding potential, likely due to having four LIF binding domains present. Both engineered Fc fusions show greater multi-LIF binding when compared to the anti-LIF mAb, L1, potentially due to higher affinity. Overall, these results imply that as Fc-fusions, inhibitors are able to bind to LIF with a 2:1 LIF:inhibitor stoichiometry, giving them the potential for greater therapeutic benefit through multi-LIF binding and sequestration.

Example 6—Competitive LIF Binding Assay

A binding assay was performed as schematically illustrated in FIG. 12, panel A to determine how well receptor decoys bound to LIF remain bound to LIF in the presence of excess soluble LIF competitor. The goal was to determine whether engineering receptors leads to a slower off-rate, as would be indicated by an improved resistance to competition by excess competitor. According to the assay, LIF is displayed on the surface of yeast. Fc-fusion inhibitors (LIFR-VPRVVAID-Fc depicted) are introduced at saturating concentrations, allowed to bind to the displayed ligand, and excess is washed away. Soluble LIF-His is then co-incubated with Fc-fusion-bound yeast. Fc-fusion binding is detected via the Fc domain of the inhibitor, which will be competed away from the yeast-displayed LIF by high concentrations of soluble LIF-His.

Results of the competitive LIF binding assay are shown in FIG. 12, panel B. LIF was displayed on yeast with LIFR-WT-Fc, LIFR-VPRVVAID-Fc, LIFR-gp130 Fusion-Fc, or the anti-LIF mAb, L1, added as a binding partner. Excess inhibitor was washed away and soluble LIF was added as a competitor for 24 hours. Fluorescent emission from an anti-Fc fluorescent antibody in each condition was normalized to controls where excess inhibitor was not removed and soluble LIF was not added.

From these results, it is determined engineered LIFR-Fc and LIFR-gp130 Fusion-Fc have dramatically improved off-rates, when compared with LIFR-WT-Fc. This is most striking in the presence of high levels of LIF-His competitor (100 nM), where engineered receptors remain over 50% bound, while LIFR-WT-Fc is almost completely competed away from yeast-displayed LIF. The relative amount of Fc-fusion that remains bound is comparable to the anti-LIF mAb, L1. Improved off-rate demonstrated by engineered Fc-fusions likely partially explains improved affinity and should lead to greater therapeutic efficacy.

Example 7—Simultaneous Receptor Binding Assay

A binding assay was performed as schematically illustrated in FIG. 13, panel A to determine if the receptor decoys bound to LIF can also simultaneously engage gp130 or LIFR. The goal was to demonstrate whether inhibitors are competitive with LIFR, gp130 or both in binding to LIF. According to the assay, gp130 (depicted) or LIFR are displayed on the surface of yeast. LIF is introduced at saturating concentrations, allowed to bind to the displayed receptor, and excess is washed away. Inhibitors (LIFR-VPRVVAID-Fc depicted) are then co-incubated with LIF-bound yeast. Binding is detected via the Fc domain of the inhibitor, which should only be present if simultaneous receptor binding occurs, using LIF as a 'bridge.' If no inhibitor binding is detected, it is determined that the displayed receptor is competitive with the co-incubated inhibitor, and thus preventing the inhibitor's binding to LIF.

Results of the simultaneous binding assay are shown in FIG. 13, panel B. Either LIFR or gp130 were displayed on yeast with human LIF used as a binding bridge. Fluorescent emission is the readout of anti-Fc fluorescent antibody, normalized to no LIF added controls. LIF binding to displayed receptors was also confirmed using an anti-His6 tag fluorescent antibody (data not shown). Simultaneous binding results for LIFR-VPRVVAID-Fc, gp130-ELDME-Fc, LIFR-gp130 heterodimeric Fc, LIFR-gp130 homodimeric Fusion-Fc, Anti-LIF mAb L1, and Anti-LIF mAb G1 are shown.

From these results, it is determined that LIFR-Fc can bind to the LIF-gp130 complex (and to a much lesser degree, and somewhat surprisingly, with the LIF-LIFR complex), while gp130-Fc can only bind to the LIF-LIFR complex. This means that LIFR-Fc effectively blocks LIFR from binding LIF, while gp130-Fc blocks gp130 from binding LIF. Polypeptides with both receptors (Heterodimeric-Fc and Fusion-Fc) show simultaneous binding to both displayed receptors to a relatively equal degree. Anti-LIF monoclonal antibodies (mAbs) L1 and G1 can only bind simultaneously with one displayed receptor-LIF complex each, gp130-LIF or LIFR-LIF, respectively. This means that L1 is competitive with LIFR (as no inhibitor binding is observed when LIFR is displayed), while G1 is competitive with gp130 (as no inhibitor binding is observed when gp130 is displayed). Thus, in terms of inhibitory mechanism, L1 is comparable to LIFR-Fc, while G1 is comparable to gp130-Fc. In all cases, no binding was observed in the absence of LIF, indicating it is necessary for simultaneous binding.

Example 8—Competitive Binding Assay

A competitive binding assay was performed as schematically illustrated in FIG. 14, panel A. According to the assay, wild-type gp130 or LIFR (depicted) are displayed on the surface of yeast. Human LIF-His is introduced at saturating concentrations. Inhibitors (LIFR-VPRVVAID-Fc depicted) are then co-incubated with LIF-bound yeast, in excess. LIF binding is detected via His6-tag on LIF. The less LIF that remains bound after inhibitor incubation, the better the inhibitor is able to compete LIF away from the WT receptor.

Results of the competitive binding assay are shown in FIG. 14, panel B. Either wild-type LIFR or gp130 were displayed on yeast and saturated with human LIF-His. Fraction bound is the fluorescent emission detected from the LIF-His, normalized to No Inhibitor added. Competitive binding of LIFR-WT-Fc, gp130-ELDME-Fc (Eng.), LIFR-VPRVVAID-Fc (Eng.), LIFR-gp130 Fusion-Fc (Eng.), LIFR-gp130 Heterodimeric Fc (Eng.), Anti-LIF mAb L1, and Anti-LIF mAb G1 are shown.

From these results it is determined that wild-type LIFR-Fc competes LIF away from both wild-type LIFR and, unexpectedly, gp130. Engineered LIFR-Fc is improved over wild-type LIFR-Fc in this regard, able to potently compete LIF away from both LIFR and gp130. Engineered gp130-Fc competes LIF away from gp130 well, but expectedly has no effect on the ability of LIFR to bind LIF. Fusions of LIFR and gp130, both as homo- and heterodimers demonstrate a potent ability to compete LIF away from both LIFR and gp130, as would be expected by having both engineered receptors present in the same inhibitor. The Anti-LIF monoclonal antibodies, L1 and G1 compete LIF away effectively from only one receptor each, LIFR and gp130, respectively, but actually enhance LIF binding to the converse receptor, gp130 and LIFR, respectively.

Example 9—Blockade of Downstream LIF Signaling in HeLa Luciferase Reporter Cells LIF binds to LIFR and gp130, causing hetero-dimerization of LIFR and gp130. Dimerization results in recruitment of JAK, which phosphorylates STAT3. This results in STAT3 dimerization, nuclear entry, and activation of transcriptional programming via STAT3 Response Elements. Cell lines can be altered to contain the gene for luciferase, preceded by a STAT3 response element, such that activation of pSTAT3 leads to production of luciferase. In this situation, luciferase activity, as determined using a standard luciferase assay with luciferin, can be directly correlated with LIF signaling in the cell. FIG. 15, panel A, schematically illustrates this LIF reporter cell system in HeLa cells.

Shown in FIG. 15, panel B, are the results from a luciferase assay, where HeLa reporter cells were exposed to 0.5 nM LIF and differing concentrations of LIFR-VPRVVAID-Fc, LIFR-VPRVVAID—gp130-ELDME Fc, and LIFR-WT-Fc. Cells were incubated for 5 hours and then lysed and put through the luciferase assay. Results are normalized to no inhibitor added. FIG. 15, panel C shows results from a delayed inhibitor addition assay. According to the assay, 0.5 nM LIF is added to HeLa reporter cells for 1.5 hours, and then 5 nM, 25 nM, or 50 nM of either LIFR-VPRVVAID-Fc, LIFR-WT-Fc, or LIFR-VPRVVAID—gp130-ELDME Fc are added directly to the well. Luciferase levels are measured 20 hours after LIF addition. Results have baseline subtracted and are normalized to no inhibitor added. FIG. 15, panel D depicts LIF derived luciferase inhibition over a large range of inhibitor concentrations to determine an $IC_{50}$ for LIFR-VPRVVAID-Fc versus LIFR-WT-Fc. A 53 fold shift in improved inhibition is observed after engineering. FIG. 15, panel E utilizes the ability of the HeLa reporter cells to respond to multiple IL-6 family member cytokines, including the close relative of LIF, oncostatin-M (OSM). Cells were incubated with 0.5 nM LIF or OSM and 1 μM of either LIFR-VPRVVAID-Fc or LIFR-WT-Fc for 5 hours, and luciferase levels measured.

Collectively, these results indicate that LIFR-VPRVVAID-Fc and LIFR-VPRVVAID—gp130-ELDME Fc are able to potently reduce LIF-mediated downstream signaling, even at low concentrations, and to significantly block LIF signaling when added after LIF is already present in the media, a promising sign for a therapeutic. Both engineered inhibitors show vastly superior inhibition when compared with LIFR-WT-Fc, to the point of a 53 fold improvement in $IC_{50}$ by LIFR-VPRVVAID-Fc over LIFR-WT-Fc. Both WT and engineered LIFR-Fc show a high degree of specificity for LIF, showing no reduction in OSM-derived luciferase signal, even at high receptor concentrations, and despite the fact that OSM can bind to LIFR. The fact that the engineered inhibitor is even more selective for LIF than WT due to its higher affinity is an indication that there will likely be no off-target toxicity associated with the engineered trap as a therapeutic.

Example 10—Ablation of LIF Signaling in Pancreatic Cancer Cells

LIF binds to LIFR and gp130, causing hetero-dimerization of LIFR and gp130. Dimerization results in recruitment of JAK, which phosphorylates STAT3 on tyrosine 705. This results in STAT3 dimerization, nuclear entry, and activation of transcriptional programming. Thus, pSTAT3-Y705 is a read-out of LIF signaling. FIG. 16, panel A, schematically illustrates LIF signaling.

Shown in FIG. 16, panel B, are Western blot results of lysates from PANC1 (human pancreatic cancer cell line) exposed to 135 pM human LIF and differing concentrations of LIFR-VPRVVAID-Fc (“LIFR Fc Eng”), LIFR-WT-Fc (“LIFR Fc WT”), LIFR-VPRVVAID—gp130-ELDME Fc (“Fusion Fc Eng”), and L1 Anti-LIF mAb (“Anti-LIF mAb”). Cells were incubated for 20 minutes at 37° C. before being lysed in the presence of protease and phosphatase inhibitors. Protein concentrations were normalized and run on a gel via SDS-PAGE. Staining for phospho-STAT3 (Y705), STAT3 (total), and β-Tubulin was carried out in the Western blot. FIG. 16, panel C, shows quantification of pSTAT3 signal, normalized to tubulin signal.

These results indicate that LIFR-VPRVVAID-Fc and LIFR-VPRVVAID—gp130-ELDME Fc are able to reduce LIF-mediated pSTAT3 levels in cancer cells, even when incubated in only ~3 fold excess, and to completely ablate LIF signaling when incubated at greater excess, as would be relevant therapeutically. The degree of inhibition is improved over the Anti-LIF mAb, L1, as shown in the quantification (panel C). LIFR-WT-Fc is much less effective at blocking LIF derived signaling, demonstrating the benefits accrued via affinity engineering. Potent signal inhibition was also observed in KP4 human pancreatic cancer cells, not shown.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A soluble leukemia inhibitory factor receptor (LIFR) polypeptide comprising an amino acid sequence that is at least 95% identical to SEQ ID NO:2, wherein the LIFR polypeptide exhibits increased binding affinity for leukemia inhibitory factor (LIF) relative to a corresponding wild-type LIFR polypeptide, wherein the soluble LIFR polypeptide comprises the amino acid substitutions L218P, H240R, I257V, V262A, T273I and N277D, and wherein numbering of positions is according to SEQ ID NO:2.

2. The soluble LIFR polypeptide of claim 1, further comprising the amino acid substitutions I217V and I260V.

3. The soluble LIFR polypeptide of claim 1, wherein the soluble LIFR polypeptide is fused to one or more heterologous polypeptides.

4. The soluble LIFR polypeptide of claim 3, wherein the one or more heterologous polypeptides comprises a heterologous polypeptide selected from the group consisting of: an Fc domain, an albumin, a transferrin, XTEN, a homo-amino acid polymer, a proline-alanine-serine polymer, an elastin-like peptide, and any combination thereof.

5. The soluble LIFR polypeptide of claim 4, wherein the one or more heterologous polypeptides comprises an Fc domain.

6. The soluble LIFR polypeptide of claim 3, wherein the one or more heterologous polypeptides comprises a soluble glycoprotein 130 (gp130) polypeptide comprising an amino acid sequence that is at least 90% identical to SEQ ID NO:4, wherein the gp130 polypeptide exhibits increased binding affinity for leukemia inhibitory factor (LIF) relative to a corresponding wild-type gp130 polypeptide, and wherein the soluble LIFR polypeptide and soluble gp130 polypeptide are fused via a linker.

7. The soluble LIFR polypeptide of claim 1, dimerized with a second soluble LIFR polypeptide of claim 1.

8. The soluble LIFR polypeptide of claim 7, wherein each soluble LIFR polypeptide is fused to an Fc domain, and wherein dimerization is via the Fc domains.

9. A nucleic acid encoding the soluble LIFR polypeptide of claim 1.

10. A cell comprising the nucleic acid of claim 9.

11. A pharmaceutical composition, comprising:

the soluble LIFR polypeptide of claim 1; and a pharmaceutically-acceptable carrier.

12. A method of treating a cancer associated with LIF signaling in an individual in need thereof, the method comprising administering a therapeutically effective amount of the pharmaceutical composition of claim 11 to the individual.

13. The method according to claim 12, wherein the cancer is pancreatic cancer.

14. A kit comprising:

the pharmaceutical composition of claim 11; and instructions for administering the pharmaceutical composition to an individual in need thereof.

15. The kit of claim 14, wherein the pharmaceutical composition is present in two or more unit dosages.

* * * * *

SEQUENCE LISTING

```
<160> NUMBER OF SEQ ID NOS: 10

<210> SEQ ID NO 1
<211> LENGTH: 789
<212> TYPE: PRT
<213> ORGANISM: Homo sapiens

<400> SEQUENCE: 1

Gln Lys Lys Gly Ala Pro His Asp Leu Lys Cys Val Thr Asn Asn Leu
1               5                   10                  15

Gln Val Trp Asn Cys Ser Trp Lys Ala Pro Ser Gly Thr Gly Arg Gly
            20                  25                  30

Thr Asp Tyr Glu Val Cys Ile Glu Asn Arg Ser Arg Ser Cys Tyr Gln
        35                  40                  45

Leu Glu Lys Thr Ser Ile Lys Ile Pro Ala Leu Ser His Gly Asp Tyr
    50                  55                  60

Glu Ile Thr Ile Asn Ser Leu His Asp Phe Gly Ser Ser Thr Ser Lys
65                  70                  75                  80

Phe Thr Leu Asn Glu Gln Asn Val Ser Leu Ile Pro Asp Thr Pro Glu
                85                  90                  95

Ile Leu Asn Leu Ser Ala Asp Phe Ser Thr Ser Thr Leu Tyr Leu Lys
            100                 105                 110

Trp Asn Asp Arg Gly Ser Val Phe Pro His Arg Ser Asn Val Ile Trp
        115                 120                 125

Glu Ile Lys Val Leu Arg Lys Glu Ser Met Glu Leu Val Lys Leu Val
    130                 135                 140

Thr His Asn Thr Thr Leu Asn Gly Lys Asp Thr Leu His His Trp Ser
145                 150                 155                 160

Trp Ala Ser Asp Met Pro Leu Glu Cys Ala Ile His Phe Val Glu Ile
                165                 170                 175

Arg Cys Tyr Ile Asp Asn Leu His Phe Ser Gly Leu Glu Glu Trp Ser
            180                 185                 190

Asp Trp Ser Pro Val Lys Asn Ile Ser Trp Ile Pro Asp Ser Gln Thr
        195                 200                 205

Lys Val Phe Pro Gln Asp Lys Val Ile Leu Val Gly Ser Asp Ile Thr
    210                 215                 220

Phe Cys Cys Val Ser Gln Glu Lys Val Leu Ser Ala Leu Ile Gly His
225                 230                 235                 240

Thr Asn Cys Pro Leu Ile His Leu Asp Gly Glu Asn Val Ala Ile Lys
                245                 250                 255

Ile Arg Asn Ile Ser Val Ser Ala Ser Ser Gly Thr Asn Val Val Phe
            260                 265                 270

Thr Thr Glu Asp Asn Ile Phe Gly Thr Val Ile Phe Ala Gly Tyr Pro
```

-continued

```
        275                 280                 285

Pro Asp Thr Pro Gln Gln Leu Asn Cys Glu Thr His Asp Leu Lys Glu
    290                 295                 300

Ile Ile Cys Ser Trp Asn Pro Gly Arg Val Thr Ala Leu Val Gly Pro
305                 310                 315                 320

Arg Ala Thr Ser Tyr Thr Leu Val Glu Ser Phe Ser Gly Lys Tyr Val
                325                 330                 335

Arg Leu Lys Arg Ala Glu Ala Pro Thr Asn Glu Ser Tyr Gln Leu Leu
            340                 345                 350

Phe Gln Met Leu Pro Asn Gln Glu Ile Tyr Asn Phe Thr Leu Asn Ala
        355                 360                 365

His Asn Pro Leu Gly Arg Ser Gln Ser Thr Ile Leu Val Asn Ile Thr
    370                 375                 380

Glu Lys Val Tyr Pro His Thr Pro Thr Ser Phe Lys Val Lys Asp Ile
385                 390                 395                 400

Asn Ser Thr Ala Val Lys Leu Ser Trp His Leu Pro Gly Asn Phe Ala
                405                 410                 415

Lys Ile Asn Phe Leu Cys Glu Ile Glu Ile Lys Lys Ser Asn Ser Val
            420                 425                 430

Gln Glu Gln Arg Asn Val Thr Ile Lys Gly Val Glu Asn Ser Ser Tyr
        435                 440                 445

Leu Val Ala Leu Asp Lys Leu Asn Pro Tyr Thr Leu Tyr Thr Phe Arg
    450                 455                 460

Ile Arg Cys Ser Thr Glu Thr Phe Trp Lys Trp Ser Lys Trp Ser Asn
465                 470                 475                 480

Lys Lys Gln His Leu Thr Thr Glu Ala Ser Pro Ser Lys Gly Pro Asp
                485                 490                 495

Thr Trp Arg Glu Trp Ser Ser Asp Gly Lys Asn Leu Ile Ile Tyr Trp
            500                 505                 510

Lys Pro Leu Pro Ile Asn Glu Ala Asn Gly Lys Ile Leu Ser Tyr Asn
        515                 520                 525

Val Ser Cys Ser Ser Asp Glu Glu Thr Gln Ser Leu Ser Glu Ile Pro
    530                 535                 540

Asp Pro Gln His Lys Ala Glu Ile Arg Leu Asp Lys Asn Asp Tyr Ile
545                 550                 555                 560

Ile Ser Val Val Ala Lys Asn Ser Val Gly Ser Ser Pro Pro Ser Lys
                565                 570                 575

Ile Ala Ser Met Glu Ile Pro Asn Asp Asp Leu Lys Ile Glu Gln Val
            580                 585                 590

Val Gly Met Gly Lys Gly Ile Leu Leu Thr Trp His Tyr Asp Pro Asn
        595                 600                 605

Met Thr Cys Asp Tyr Val Ile Lys Trp Cys Asn Ser Ser Arg Ser Glu
    610                 615                 620

Pro Cys Leu Met Asp Trp Arg Lys Val Pro Ser Asn Ser Thr Glu Thr
625                 630                 635                 640

Val Ile Glu Ser Asp Glu Phe Arg Pro Gly Ile Arg Tyr Asn Phe Phe
                645                 650                 655

Leu Tyr Gly Cys Arg Asn Gln Gly Tyr Gln Leu Leu Arg Ser Met Ile
            660                 665                 670

Gly Tyr Ile Glu Glu Leu Ala Pro Ile Val Ala Pro Asn Phe Thr Val
        675                 680                 685

Glu Asp Thr Ser Ala Asp Ser Ile Leu Val Lys Trp Glu Asp Ile Pro
    690                 695                 700
```

Val Glu Glu Leu Arg Gly Phe Leu Arg Gly Tyr Leu Phe Tyr Phe Gly
705 710 715 720

Lys Gly Glu Arg Asp Thr Ser Lys Met Arg Val Leu Glu Ser Gly Arg
725 730 735

Ser Asp Ile Lys Val Lys Asn Ile Thr Asp Ile Ser Gln Lys Thr Leu
740 745 750

Arg Ile Ala Asp Leu Gln Gly Lys Thr Ser Tyr His Leu Val Leu Arg
755 760 765

Ala Tyr Thr Asp Gly Gly Val Gly Pro Glu Lys Ser Met Tyr Val Val
770 775 780

Thr Lys Glu Asn Ser
785

<210> SEQ ID NO 2
<211> LENGTH: 490
<212> TYPE: PRT
<213> ORGANISM: Artificial Sequence
<220> FEATURE:
<223> OTHER INFORMATION: Synthetic sequence

<400> SEQUENCE: 2

Gln Lys Lys Gly Ala Pro His Asp Leu Lys Cys Val Thr Asn Asn Leu
1 5 10 15

Gln Val Trp Asn Cys Ser Trp Lys Ala Pro Ser Gly Thr Gly Arg Gly
20 25 30

Thr Asp Tyr Glu Val Cys Ile Glu Asn Arg Ser Arg Ser Cys Tyr Gln
35 40 45

Leu Glu Lys Thr Ser Ile Lys Ile Pro Ala Leu Ser His Gly Asp Tyr
50 55 60

Glu Ile Thr Ile Asn Ser Leu His Asp Phe Gly Ser Ser Thr Ser Lys
65 70 75 80

Phe Thr Leu Asn Glu Gln Asn Val Ser Leu Ile Pro Asp Thr Pro Glu
85 90 95

Ile Leu Asn Leu Ser Ala Asp Phe Ser Thr Ser Thr Leu Tyr Leu Lys
100 105 110

Trp Asn Asp Arg Gly Ser Val Phe Pro His Arg Ser Asn Val Ile Trp
115 120 125

Glu Ile Lys Val Leu Arg Lys Glu Ser Met Glu Leu Val Lys Leu Val
130 135 140

Thr His Asn Thr Thr Leu Asn Gly Lys Asp Thr Leu His His Trp Ser
145 150 155 160

Trp Ala Ser Asp Met Pro Leu Glu Cys Ala Ile His Phe Val Glu Ile
165 170 175

Arg Cys Tyr Ile Asp Asn Leu His Phe Ser Gly Leu Glu Glu Trp Ser
180 185 190

Asp Trp Ser Pro Val Lys Asn Ile Ser Trp Ile Pro Asp Ser Gln Thr
195 200 205

Lys Val Phe Pro Gln Asp Lys Val Ile Leu Val Gly Ser Asp Ile Thr
210 215 220

Phe Cys Cys Val Ser Gln Glu Lys Val Leu Ser Ala Leu Ile Gly His
225 230 235 240

Thr Asn Cys Pro Leu Ile His Leu Asp Gly Glu Asn Val Ala Ile Lys
245 250 255

Ile Arg Asn Ile Ser Val Ser Ala Ser Ser Gly Thr Asn Val Val Phe
260 265 270

```
Thr Thr Glu Asp Asn Ile Phe Gly Thr Val Ile Phe Ala Gly Tyr Pro
        275                 280                 285

Pro Asp Thr Pro Gln Gln Leu Asn Cys Glu Thr His Asp Leu Lys Glu
    290                 295                 300

Ile Ile Cys Ser Trp Asn Pro Gly Arg Val Thr Ala Leu Val Gly Pro
305                 310                 315                 320

Arg Ala Thr Ser Tyr Thr Leu Val Glu Ser Phe Ser Gly Lys Tyr Val
                325                 330                 335

Arg Leu Lys Arg Ala Glu Ala Pro Thr Asn Glu Ser Tyr Gln Leu Leu
            340                 345                 350

Phe Gln Met Leu Pro Asn Gln Glu Ile Tyr Asn Phe Thr Leu Asn Ala
        355                 360                 365

His Asn Pro Leu Gly Arg Ser Gln Ser Thr Ile Leu Val Asn Ile Thr
    370                 375                 380

Glu Lys Val Tyr Pro His Thr Pro Thr Ser Phe Lys Val Lys Asp Ile
385                 390                 395                 400

Asn Ser Thr Ala Val Lys Leu Ser Trp His Leu Pro Gly Asn Phe Ala
                405                 410                 415

Lys Ile Asn Phe Leu Cys Glu Ile Glu Ile Lys Lys Ser Asn Ser Val
            420                 425                 430

Gln Glu Gln Arg Asn Val Thr Ile Lys Gly Val Glu Asn Ser Ser Tyr
        435                 440                 445

Leu Val Ala Leu Asp Lys Leu Asn Pro Tyr Thr Leu Tyr Thr Phe Arg
    450                 455                 460

Ile Arg Cys Ser Thr Glu Thr Phe Trp Lys Trp Ser Lys Trp Ser Asn
465                 470                 475                 480

Lys Lys Gln His Leu Thr Thr Glu Ala Ser
                485                 490


<210> SEQ ID NO 3
<211> LENGTH: 597
<212> TYPE: PRT
<213> ORGANISM: Homo sapiens

<400> SEQUENCE: 3

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Arg Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
```

-continued

```
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
    290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Val Ala Thr Leu Thr Val Arg Asn Leu Val
    370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
        435                 440                 445

Gln Gln Glu Asp Gly Thr Val His Arg Thr Tyr Leu Arg Gly Asn Leu
    450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
        515                 520                 525

Ile Arg Asn Tyr Thr Ile Phe Tyr Arg Thr Ile Ile Gly Asn Glu Thr
    530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575
```

```
Gly Gly Lys Asp Gly Pro Glu Phe Thr Phe Thr Thr Pro Lys Phe Ala
            580                 585                 590

Gln Gly Glu Ile Glu
        595


<210> SEQ ID NO 4
<211> LENGTH: 201
<212> TYPE: PRT
<213> ORGANISM: Artificial Sequence
<220> FEATURE:
<223> OTHER INFORMATION: Synthetic sequence

<400> SEQUENCE: 4

Leu Pro Pro Glu Lys Pro Lys Asn Leu Ser Cys Ile Val Asn Glu Gly
1               5                   10                  15

Lys Lys Met Arg Cys Glu Trp Asp Arg Gly Arg Glu Thr His Leu Glu
            20                  25                  30

Thr Asn Phe Thr Leu Lys Ser Glu Trp Ala Thr His Lys Phe Ala Asp
        35                  40                  45

Cys Lys Ala Lys Arg Asp Thr Pro Thr Ser Cys Thr Val Asp Tyr Ser
    50                  55                  60

Thr Val Tyr Phe Val Asn Ile Glu Val Trp Val Glu Ala Glu Asn Ala
65                  70                  75                  80

Leu Gly Lys Val Thr Ser Asp His Ile Asn Phe Asp Pro Val Tyr Lys
                85                  90                  95

Val Lys Pro Asn Pro Pro His Asn Leu Ser Val Ile Asn Ser Glu Glu
            100                 105                 110

Leu Ser Ser Ile Leu Lys Leu Thr Trp Thr Asn Pro Ser Ile Lys Ser
        115                 120                 125

Val Ile Ile Leu Lys Tyr Asn Ile Gln Tyr Arg Thr Lys Asp Ala Ser
    130                 135                 140

Thr Trp Ser Gln Ile Pro Pro Glu Asp Thr Ala Ser Thr Arg Ser Ser
145                 150                 155                 160

Phe Thr Val Gln Asp Leu Lys Pro Phe Thr Glu Tyr Val Phe Arg Ile
                165                 170                 175

Arg Cys Met Lys Glu Asp Gly Lys Gly Tyr Trp Ser Asp Trp Ser Glu
            180                 185                 190

Glu Ala Ser Gly Ile Thr Tyr Glu Asp
        195                 200


<210> SEQ ID NO 5
<211> LENGTH: 227
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 6
<211> LENGTH: 434
<212> TYPE: PRT
<213> ORGANISM: Artificial Sequence
<220> FEATURE:
<223> OTHER INFORMATION: Synthetic sequence

<400> SEQUENCE: 6

Leu Pro Pro Glu Lys Pro Lys Asn Leu Ser Cys Ile Val Asn Glu Gly
1               5                   10                  15

Lys Lys Met Arg Cys Glu Trp Asp Arg Gly Arg Glu Thr His Leu Glu
            20                  25                  30

Thr Asn Phe Thr Leu Lys Ser Glu Trp Ala Thr His Glu Leu Ala Asp
        35                  40                  45

Cys Lys Ala Lys Arg Asp Thr Pro Thr Ser Cys Thr Val Asp Tyr Ser
    50                  55                  60

Thr Val Tyr Phe Val Asn Ile Glu Val Trp Val Glu Ala Glu Asn Ala
65                  70                  75                  80

Leu Gly Lys Val Thr Ser Asp His Ile Asn Phe Asp Pro Val Asp Lys
                85                  90                  95

Val Lys Pro Asn Pro Pro His Asn Leu Ser Val Ile Asn Ser Glu Glu
            100                 105                 110

Leu Ser Ser Ile Leu Lys Leu Thr Trp Thr Asn Pro Ser Ile Lys Ser
        115                 120                 125

Val Met Ile Leu Lys Tyr Asn Ile Gln Tyr Arg Thr Lys Asp Ala Ser
    130                 135                 140

Thr Trp Ser Gln Ile Pro Pro Glu Asp Thr Ala Ser Thr Arg Ser Ser
145                 150                 155                 160

Phe Thr Val Gln Asp Leu Lys Pro Phe Thr Glu Tyr Val Phe Arg Ile
                165                 170                 175

Arg Cys Met Lys Glu Asp Gly Glu Gly Tyr Trp Ser Asp Trp Ser Glu
            180                 185                 190

Glu Ala Ser Gly Ile Thr Tyr Glu Asp Gly Ser Gly Ser Gly Ser Asp
        195                 200                 205
```

```
Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Gln Val Lys Phe Asn Trp Tyr Val Asp Gly Val Gln Val His
            260                 265                 270

Asn Ala Lys Thr Lys Pro Arg Glu Gln Gln Tyr Asn Ser Thr Tyr Arg
        275                 280                 285

Val Val Ser Val Leu Thr Val Leu His Gln Asn Trp Leu Asp Gly Lys
    290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Glu Glu Met Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys


<210> SEQ ID NO 7
<211> LENGTH: 725
<212> TYPE: PRT
<213> ORGANISM: Artificial Sequence
<220> FEATURE:
<223> OTHER INFORMATION: Synthetic sequence

<400> SEQUENCE: 7

Gln Lys Lys Gly Ala Pro His Asp Leu Lys Cys Val Thr Asn Asn Leu
1               5                   10                  15

Gln Val Trp Asn Cys Ser Trp Lys Ala Pro Ser Gly Thr Gly Arg Gly
            20                  25                  30

Thr Asp Tyr Glu Val Cys Ile Glu Asn Arg Ser Arg Ser Cys Tyr Gln
        35                  40                  45

Leu Glu Lys Thr Ser Ile Lys Ile Pro Ala Leu Ser His Gly Asp Tyr
    50                  55                  60

Glu Ile Thr Ile Asn Ser Leu His Asp Phe Gly Ser Ser Thr Ser Lys
65                  70                  75                  80

Phe Thr Leu Asn Glu Gln Asn Val Ser Leu Ile Pro Asp Thr Pro Glu
                85                  90                  95

Ile Leu Asn Leu Ser Ala Asp Phe Ser Thr Ser Thr Leu Tyr Leu Lys
            100                 105                 110

Trp Asn Asp Arg Gly Ser Val Phe Pro His Arg Ser Asn Val Ile Trp
        115                 120                 125

Glu Ile Lys Val Leu Arg Lys Glu Ser Met Glu Leu Val Lys Leu Val
```

-continued

```
    130                 135                 140

Thr His Asn Thr Thr Leu Asn Gly Lys Asp Thr Leu His His Trp Ser
145                 150                 155                 160

Trp Ala Ser Asp Met Pro Leu Glu Cys Ala Ile His Phe Val Glu Ile
                165                 170                 175

Arg Cys Tyr Ile Asp Asn Leu His Phe Ser Gly Leu Glu Glu Trp Ser
            180                 185                 190

Asp Trp Ser Pro Val Lys Asn Ile Ser Trp Ile Pro Asp Ser Gln Thr
        195                 200                 205

Lys Val Phe Pro Gln Asp Lys Val Val Pro Val Gly Ser Asp Ile Thr
    210                 215                 220

Phe Cys Cys Val Ser Gln Glu Lys Val Leu Ser Ala Leu Ile Gly Arg
225                 230                 235                 240

Thr Asp Cys Pro Leu Ile His Leu Asp Gly Glu Asn Val Ala Ile Lys
                245                 250                 255

Val Arg Asn Val Ser Ala Ser Ala Ser Ser Gly Thr Asn Val Val Phe
            260                 265                 270

Ile Thr Glu Asp Asp Ile Phe Gly Thr Val Ile Phe Ala Gly Tyr Pro
        275                 280                 285

Pro Asp Thr Pro Gln Gly Ser Gln Leu Asn Cys Glu Thr His Asp Leu
    290                 295                 300

Lys Glu Ile Ile Cys Ser Trp Asn Pro Gly Arg Val Thr Ala Leu Val
305                 310                 315                 320

Gly Pro Arg Ala Thr Ser Tyr Thr Leu Val Glu Ser Phe Ser Gly Lys
                325                 330                 335

Tyr Val Arg Leu Lys Arg Ala Glu Ala Pro Thr Asn Glu Ser Tyr Gln
            340                 345                 350

Leu Leu Phe Gln Met Leu Pro Asn Gln Glu Ile Tyr Asn Phe Thr Leu
        355                 360                 365

Asn Ala His Asn Pro Leu Gly Arg Ser Gln Ser Thr Ile Leu Val Asn
    370                 375                 380

Ile Thr Glu Lys Val Tyr Pro His Thr Pro Thr Ser Phe Lys Val Lys
385                 390                 395                 400

Asp Ile Asn Ser Thr Ala Val Lys Leu Ser Trp His Leu Pro Gly Asn
                405                 410                 415

Phe Ala Lys Ile Asn Phe Leu Cys Glu Ile Glu Ile Lys Lys Ser Asn
            420                 425                 430

Ser Val Gln Glu Gln Arg Asn Val Thr Ile Lys Gly Val Glu Asn Ser
        435                 440                 445

Ser Tyr Leu Val Ala Leu Asp Lys Leu Asn Pro Tyr Thr Leu Tyr Thr
    450                 455                 460

Phe Arg Ile Arg Cys Ser Thr Glu Thr Phe Trp Lys Trp Ser Lys Trp
465                 470                 475                 480

Ser Asn Lys Lys Gln His Leu Thr Thr Glu Ala Ser Gly Ser Gly Ser
                485                 490                 495

Gly Ser Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
        515                 520                 525

Leu Met Ile Ser Arg Thr Pro Glu Val Thr Cys Val Val Val Asp Val
    530                 535                 540

Ser His Glu Asp Pro Gln Val Lys Phe Asn Trp Tyr Val Asp Gly Val
545                 550                 555                 560
```

-continued

```
Gln Val His Asn Ala Lys Thr Lys Pro Arg Glu Gln Gln Tyr Asn Ser
                565                 570                 575

Thr Tyr Arg Val Val Ser Val Leu Thr Val Leu His Gln Asn Trp Leu
            580                 585                 590

Asp Gly Lys Glu Tyr Lys Cys Lys Val Ser Asn Lys Ala Leu Pro Ala
        595                 600                 605

Pro Ile Glu Lys Thr Ile Ser Lys Ala Lys Gly Gln Pro Arg Glu Pro
    610                 615                 620

Gln Val Tyr Thr Leu Pro Pro Ser Arg Glu Glu Met Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly Lys
                725


<210> SEQ ID NO 8
<211> LENGTH: 949
<212> TYPE: PRT
<213> ORGANISM: Artificial Sequence
<220> FEATURE:
<223> OTHER INFORMATION: Synthetic sequence

<400> SEQUENCE: 8

Gln Lys Lys Gly Ala Pro His Asp Leu Lys Cys Val Thr Asn Asn Leu
1               5                   10                  15

Gln Val Trp Asn Cys Ser Trp Lys Ala Pro Ser Gly Thr Gly Arg Gly
            20                  25                  30

Thr Asp Tyr Glu Val Cys Ile Glu Asn Arg Ser Arg Ser Cys Tyr Gln
        35                  40                  45

Leu Glu Lys Thr Ser Ile Lys Ile Pro Ala Leu Ser His Gly Asp Tyr
    50                  55                  60

Glu Ile Thr Ile Asn Ser Leu His Asp Phe Gly Ser Ser Thr Ser Lys
65                  70                  75                  80

Phe Thr Leu Asn Glu Gln Asn Val Ser Leu Ile Pro Asp Thr Pro Glu
                85                  90                  95

Ile Leu Asn Leu Ser Ala Asp Phe Ser Thr Ser Thr Leu Tyr Leu Lys
            100                 105                 110

Trp Asn Asp Arg Gly Ser Val Phe Pro His Arg Ser Asn Val Ile Trp
        115                 120                 125

Glu Ile Lys Val Leu Arg Lys Glu Ser Met Glu Leu Val Lys Leu Val
    130                 135                 140

Thr His Asn Thr Thr Leu Asn Gly Lys Asp Thr Leu His His Trp Ser
145                 150                 155                 160

Trp Ala Ser Asp Met Pro Leu Glu Cys Ala Ile His Phe Val Glu Ile
                165                 170                 175

Arg Cys Tyr Ile Asp Asn Leu His Phe Ser Gly Leu Glu Glu Trp Ser
            180                 185                 190
```

-continued

```
Asp Trp Ser Pro Val Lys Asn Ile Ser Trp Ile Pro Asp Ser Gln Thr
        195                 200                 205

Lys Val Phe Pro Gln Asp Lys Val Val Pro Val Gly Ser Asp Ile Thr
    210                 215                 220

Phe Cys Cys Val Ser Gln Glu Lys Val Leu Ser Ala Leu Ile Gly Arg
225                 230                 235                 240

Thr Asn Cys Pro Leu Ile His Leu Asp Gly Glu Asn Val Ala Ile Lys
                245                 250                 255

Val Arg Asn Val Ser Ala Ser Ala Ser Ser Gly Thr Asn Val Val Phe
            260                 265                 270

Ile Thr Glu Asp Asp Ile Phe Gly Thr Val Ile Phe Ala Gly Tyr Pro
        275                 280                 285

Pro Asp Thr Pro Gln Gln Leu Asn Cys Glu Thr His Asp Leu Lys Glu
    290                 295                 300

Ile Ile Cys Ser Trp Asn Pro Gly Arg Val Thr Ala Leu Val Gly Pro
305                 310                 315                 320

Arg Ala Thr Ser Tyr Thr Leu Val Glu Ser Phe Ser Gly Lys Tyr Val
                325                 330                 335

Arg Leu Lys Arg Ala Glu Ala Pro Thr Asn Glu Ser Tyr Gln Leu Leu
            340                 345                 350

Phe Gln Met Leu Pro Asn Gln Glu Ile Tyr Asn Phe Thr Leu Asn Ala
        355                 360                 365

His Asn Pro Leu Gly Arg Ser Gln Ser Thr Ile Leu Val Asn Ile Thr
    370                 375                 380

Glu Lys Val Tyr Pro His Thr Pro Thr Ser Phe Lys Val Lys Asp Ile
385                 390                 395                 400

Asn Ser Thr Ala Val Lys Leu Ser Trp His Leu Pro Gly Asn Phe Ala
                405                 410                 415

Lys Ile Asn Phe Leu Cys Glu Ile Glu Ile Lys Lys Ser Asn Ser Val
            420                 425                 430

Gln Glu Gln Arg Asn Val Thr Ile Lys Gly Val Glu Asn Ser Ser Tyr
        435                 440                 445

Leu Val Ala Leu Asp Lys Leu Asn Pro Tyr Thr Leu Tyr Thr Phe Arg
    450                 455                 460

Ile Arg Cys Ser Thr Glu Thr Phe Trp Lys Trp Ser Lys Trp Ser Asn
465                 470                 475                 480

Lys Lys Gln His Leu Thr Thr Glu Ala Ser Gly Gly Gly Gly Ser Gly
                485                 490                 495

Gly Gly Gly Ser Gly Gly Gly Gly Ser Gly Gly Gly Gly Ser Gly Gly
            500                 505                 510

Gly Gly Ser Leu Pro Pro Glu Lys Pro Lys Asn Leu Ser Cys Ile Val
        515                 520                 525

Asn Glu Gly Lys Lys Met Arg Cys Glu Trp Asp Arg Gly Arg Glu Thr
    530                 535                 540

His Leu Glu Thr Asn Phe Thr Leu Lys Ser Glu Trp Ala Thr His Glu
545                 550                 555                 560

Leu Ala Asp Cys Lys Ala Lys Arg Asp Thr Pro Thr Ser Cys Thr Val
                565                 570                 575

Asp Tyr Ser Thr Val Tyr Phe Val Asn Ile Glu Val Trp Val Glu Ala
            580                 585                 590

Glu Asn Ala Leu Gly Lys Val Thr Ser Asp His Ile Asn Phe Asp Pro
        595                 600                 605
```

```
Val Asp Lys Val Lys Pro Asn Pro Pro His Asn Leu Ser Val Ile Asn
    610                 615                 620

Ser Glu Glu Leu Ser Ser Ile Leu Lys Leu Thr Trp Thr Asn Pro Ser
625                 630                 635                 640

Ile Lys Ser Val Met Ile Leu Lys Tyr Asn Ile Gln Tyr Arg Thr Lys
                645                 650                 655

Asp Ala Ser Thr Trp Ser Gln Ile Pro Pro Glu Asp Thr Ala Ser Thr
            660                 665                 670

Arg Ser Ser Phe Thr Val Gln Asp Leu Lys Pro Phe Thr Glu Tyr Val
        675                 680                 685

Phe Arg Ile Arg Cys Met Lys Glu Asp Gly Glu Gly Tyr Trp Ser Asp
    690                 695                 700

Trp Ser Glu Glu Ala Ser Gly Ile Thr Tyr Glu Asp Gly Ser Gly Ser
705                 710                 715                 720

Gly Ser Asp Lys Thr His Thr Cys Pro Pro Cys Pro Ala Pro Glu Leu
                725                 730                 735

Leu Gly Gly Pro Ser Val Phe Leu Phe Pro Pro Lys Pro Lys Asp Thr
            740                 745                 750

Leu Met Ile Ser Arg Thr Pro Glu Val Thr Cys Val Val Val Asp Val
        755                 760                 765

Ser His Glu Asp Pro Gln Val Lys Phe Asn Trp Tyr Val Asp Gly Val
    770                 775                 780

Gln Val His Asn Ala Lys Thr Lys Pro Arg Glu Gln Gln Tyr Asn Ser
785                 790                 795                 800

Thr Tyr Arg Val Val Ser Val Leu Thr Val Leu His Gln Asn Trp Leu
                805                 810                 815

Asp Gly Lys Glu Tyr Lys Cys Lys Val Ser Asn Lys Ala Leu Pro Ala
            820                 825                 830

Pro Ile Glu Lys Thr Ile Ser Lys Ala Lys Gly Gln Pro Arg Glu Pro
        835                 840                 845

Gln Val Tyr Thr Leu Pro Pro Ser Arg Glu Glu Met Thr Lys Asn Gln
    850                 855                 860

Val Ser Leu Thr Cys Leu Val Lys Gly Phe Tyr Pro Ser Asp Ile Ala
865                 870                 875                 880

Val Glu Trp Glu Ser Asn Gly Gln Pro Glu Asn Asn Tyr Lys Thr Thr
                885                 890                 895

Pro Pro Val Leu Asp Ser Asp Gly Ser Phe Phe Leu Tyr Ser Lys Leu
            900                 905                 910

Thr Val Asp Lys Ser Arg Trp Gln Gln Gly Asn Val Phe Ser Cys Ser
        915                 920                 925

Val Met His Glu Ala Leu His Asn His Tyr Thr Gln Lys Ser Leu Ser
    930                 935                 940

Leu Ser Pro Gly Lys
945
```

<210> SEQ ID NO 9
<211> LENGTH: 723
<212> TYPE: PRT
<213> ORGANISM: Artificial Sequence
<220> FEATURE:
<223> OTHER INFORMATION: Synthetic sequence

<400> SEQUENCE: 9

```
Gln Lys Lys Gly Ala Pro His Asp Leu Lys Cys Val Thr Asn Asn Leu
1               5                   10                  15
```

-continued

```
Gln Val Trp Asn Cys Ser Trp Lys Ala Pro Ser Gly Thr Gly Arg Gly
            20                  25                  30

Thr Asp Tyr Glu Val Cys Ile Glu Asn Arg Ser Arg Ser Cys Tyr Gln
        35                  40                  45

Leu Glu Lys Thr Ser Ile Lys Ile Pro Ala Leu Ser His Gly Asp Tyr
    50                  55                  60

Glu Ile Thr Ile Asn Ser Leu His Asp Phe Gly Ser Ser Thr Ser Lys
65                  70                  75                  80

Phe Thr Leu Asn Glu Gln Asn Val Ser Leu Ile Pro Asp Thr Pro Glu
                85                  90                  95

Ile Leu Asn Leu Ser Ala Asp Phe Ser Thr Ser Thr Leu Tyr Leu Lys
            100                 105                 110

Trp Asn Asp Arg Gly Ser Val Phe Pro His Arg Ser Asn Val Ile Trp
        115                 120                 125

Glu Ile Lys Val Leu Arg Lys Glu Ser Met Glu Leu Val Lys Leu Val
    130                 135                 140

Thr His Asn Thr Thr Leu Asn Gly Lys Asp Thr Leu His His Trp Ser
145                 150                 155                 160

Trp Ala Ser Asp Met Pro Leu Glu Cys Ala Ile His Phe Val Glu Ile
                165                 170                 175

Arg Cys Tyr Ile Asp Asn Leu His Phe Ser Gly Leu Glu Glu Trp Ser
            180                 185                 190

Asp Trp Ser Pro Val Lys Asn Ile Ser Trp Ile Pro Asp Ser Gln Thr
        195                 200                 205

Lys Val Phe Pro Gln Asp Lys Val Val Pro Val Gly Ser Asp Ile Thr
    210                 215                 220

Phe Cys Cys Val Ser Gln Glu Lys Val Leu Ser Ala Leu Ile Gly Arg
225                 230                 235                 240

Thr Asp Cys Pro Leu Ile His Leu Asp Gly Glu Asn Val Ala Ile Lys
                245                 250                 255

Val Arg Asn Val Ser Ala Ser Ala Ser Ser Gly Thr Asn Val Val Phe
            260                 265                 270

Ile Thr Glu Asp Asp Ile Phe Gly Thr Val Ile Phe Ala Gly Tyr Pro
        275                 280                 285

Pro Asp Thr Pro Gln Gln Leu Asn Cys Glu Thr His Asp Leu Lys Glu
    290                 295                 300

Ile Ile Cys Ser Trp Asn Pro Gly Arg Val Thr Ala Leu Val Gly Pro
305                 310                 315                 320

Arg Ala Thr Ser Tyr Thr Leu Val Glu Ser Phe Ser Gly Lys Tyr Val
                325                 330                 335

Arg Leu Lys Arg Ala Glu Ala Pro Thr Asn Glu Ser Tyr Gln Leu Leu
            340                 345                 350

Phe Gln Met Leu Pro Asn Gln Glu Ile Tyr Asn Phe Thr Leu Asn Ala
        355                 360                 365

His Asn Pro Leu Gly Arg Ser Gln Ser Thr Ile Leu Val Asn Ile Thr
    370                 375                 380

Glu Lys Val Tyr Pro His Thr Pro Thr Ser Phe Lys Val Lys Asp Ile
385                 390                 395                 400

Asn Ser Thr Ala Val Lys Leu Ser Trp His Leu Pro Gly Asn Phe Ala
                405                 410                 415

Lys Ile Asn Phe Leu Cys Glu Ile Glu Ile Lys Lys Ser Asn Ser Val
            420                 425                 430

Gln Glu Gln Arg Asn Val Thr Ile Lys Gly Val Glu Asn Ser Ser Tyr
```

```
        435                 440                 445

Leu Val Ala Leu Asp Lys Leu Asn Pro Tyr Thr Leu Tyr Thr Phe Arg
    450                 455                 460

Ile Arg Cys Ser Thr Glu Thr Phe Trp Lys Trp Ser Lys Trp Ser Asn
465                 470                 475                 480

Lys Lys Gln His Leu Thr Thr Glu Ala Ser Gly Ser Gly Ser Gly Ser
                485                 490                 495

Asp Lys Thr His Thr Cys Pro Pro Cys Pro Ala Pro Glu Leu Leu Gly
            500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
    530                 535                 540

Glu Asp Pro Gln Val Lys Phe Asn Trp Tyr Val Asp Gly Val Gln Val
545                 550                 555                 560

His Asn Ala Lys Thr Lys Pro Arg Glu Gln Gln Tyr Asn Ser Thr Tyr
                565                 570                 575

Arg Val Val Ser Val Leu Thr Val Leu His Gln Asn Trp Leu Asp Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Glu Glu Met Thr Lys Asn Gln Val Ser
625                 630                 635                 640

Leu Trp Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly Lys


<210> SEQ ID NO 10
<211> LENGTH: 434
<212> TYPE: PRT
<213> ORGANISM: Artificial Sequence
<220> FEATURE:
<223> OTHER INFORMATION: Synthetic sequence

<400> SEQUENCE: 10

Leu Pro Pro Glu Lys Pro Lys Asn Leu Ser Cys Ile Val Asn Glu Gly
1               5                   10                  15

Lys Lys Met Arg Cys Glu Trp Asp Arg Gly Arg Glu Thr His Leu Glu
            20                  25                  30

Thr Asn Phe Thr Leu Lys Ser Glu Trp Ala Thr His Glu Leu Ala Asp
        35                  40                  45

Cys Lys Ala Lys Arg Asp Thr Pro Thr Ser Cys Thr Val Asp Tyr Ser
    50                  55                  60

Thr Val Tyr Phe Val Asn Ile Glu Val Trp Val Glu Ala Glu Asn Ala
65                  70                  75                  80
```

-continued

```
Leu Gly Lys Val Thr Ser Asp His Ile Asn Phe Asp Pro Val Asp Lys
                85                  90                  95

Val Lys Pro Asn Pro Pro His Asn Leu Ser Val Ile Asn Ser Glu Glu
            100                 105                 110

Leu Ser Ser Ile Leu Lys Leu Thr Trp Thr Asn Pro Ser Ile Lys Ser
        115                 120                 125

Val Met Ile Leu Lys Tyr Asn Ile Gln Tyr Arg Thr Lys Asp Ala Ser
    130                 135                 140

Thr Trp Ser Gln Ile Pro Pro Glu Asp Thr Ala Ser Thr Arg Ser Ser
145                 150                 155                 160

Phe Thr Val Gln Asp Leu Lys Pro Phe Thr Glu Tyr Val Phe Arg Ile
                165                 170                 175

Arg Cys Met Lys Glu Asp Gly Glu Gly Tyr Trp Ser Asp Trp Ser Glu
            180                 185                 190

Glu Ala Ser Gly Ile Thr Tyr Glu Asp Gly Ser Gly Ser Gly Ser Asp
        195                 200                 205

Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Gln Val Lys Phe Asn Trp Tyr Val Asp Gly Val Gln Val His
            260                 265                 270

Asn Ala Lys Thr Lys Pro Arg Glu Gln Gln Tyr Asn Ser Thr Tyr Arg
        275                 280                 285

Val Val Ser Val Leu Thr Val Leu His Gln Asn Trp Leu Asp Gly Lys
    290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Glu Glu Met Thr Lys Asn Gln Val Ser Leu
            340                 345                 350

Ser Cys Ala Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Val Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys
```